(12) United States Patent
Burstein et al.

(10) Patent No.: US 9,427,560 B2
(45) Date of Patent: Aug. 30, 2016

(54) ACTIVE AGENT DELIVERY DEVICE

(75) Inventors: Pinchas Burstein, Ramat Hasharon (IL); Guy Keenan, Tel Aviv (IL); Lior Raday, D.N. Hof Ashkelon (IL); Lior Mareli, Rehovot (IL); David Daily, Herzliya (IL)

(73) Assignee: INNOVATIVE PHARMACEUTICAL COMCEPTS (IPC) INC., Road Town (VG)

( * ) Notice: Subject to any disclaimer, the term of this patent is extended or adjusted under 35 U.S.C. 154(b) by 64 days.

(21) Appl. No.: 13/816,380

(22) PCT Filed: Aug. 11, 2011

(86) PCT No.: PCT/IL2011/000657
§ 371 (c)(1),
(2), (4) Date: Feb. 11, 2013

(87) PCT Pub. No.: WO2012/020416
PCT Pub. Date: Feb. 16, 2012

(65) Prior Publication Data
US 2013/0144221 A1    Jun. 6, 2013

Related U.S. Application Data

(60) Provisional application No. 61/372,460, filed on Aug. 11, 2010.

(51) Int. Cl.
*A61F 13/00* (2006.01)
*A61M 5/178* (2006.01)
*A61F 13/40* (2006.01)
*A61M 35/00* (2006.01)

(52) U.S. Cl.
CPC .......... *A61M 35/006* (2013.01); *A61M 5/178* (2013.01); *A61M 35/003* (2013.01)

(58) Field of Classification Search
CPC .......... A61M 35/003; A61M 35/006; A61M 5/178; A61M 32/00
USPC ................................ 604/218, 228, 290, 311
See application file for complete search history.

(56) References Cited

U.S. PATENT DOCUMENTS

| 1,442,662 | A | * | 1/1923 | Guinn | ............. A46B 11/0027 132/290 |
| 3,110,309 | A | | 11/1963 | Higgins | |
| 3,481,676 | A | * | 12/1969 | Schwartzman | ........ A45D 34/04 401/134 |
| 4,030,199 | A | * | 6/1977 | Russell | ................. A61C 15/00 15/106 |

(Continued)

FOREIGN PATENT DOCUMENTS

| DE | 102007046600 A1 | 4/2009 |
| WO | 2012/020416 A2 | 2/2012 |

OTHER PUBLICATIONS

International Search Report of PCT/IL2011/000657, dated Feb. 21, 2012.

(Continued)

*Primary Examiner* — Quynh-Nhu H Vu

(57) ABSTRACT

A device for delivering an active agent to a tissue (100), comprising; a housing (10) including a reservoir (20) for containing said active agent; a delivery tip (35) being in fluid communication with said reservoir; and, a delivery mechanism (40) capable of delivering a predetermined amount of said active agent and releasing the same upon contact between said delivery tip and said tissue.

12 Claims, 28 Drawing Sheets

(56) References Cited

U.S. PATENT DOCUMENTS

| | | | | |
|---|---|---|---|---|
| 4,608,968 | A * | 9/1986 | Rosofsky | A46B 7/04 401/132 |
| 4,961,661 | A * | 10/1990 | Sutton et al. | 401/6 |
| 5,026,283 | A * | 6/1991 | Osanai | A61C 5/066 206/222 |
| 5,035,525 | A * | 7/1991 | Konose | A45D 34/042 401/205 |
| 5,042,690 | A * | 8/1991 | O'Meara | A45D 34/042 206/15.2 |
| RE33,801 | E * | 1/1992 | Green | A61C 5/066 215/DIG. 8 |
| 5,120,301 | A * | 6/1992 | Wu | A61M 35/006 401/132 |
| 5,286,257 | A * | 2/1994 | Fischer | A61C 3/005 222/136 |
| 5,342,136 | A * | 8/1994 | Fukami | B43K 8/03 401/134 |
| 5,769,553 | A * | 6/1998 | Chaudhri et al. | 401/195 |
| 6,585,511 | B2 * | 7/2003 | Dragan | A61C 5/062 401/176 |
| 7,077,826 | B1 * | 7/2006 | Gray | A61M 5/3135 604/171 |
| 7,596,974 | B2 * | 10/2009 | Smith | C11D 17/041 134/201 |
| 7,712,991 | B2 * | 5/2010 | Fontana | A45D 34/042 401/133 |
| 7,727,175 | B2 * | 6/2010 | Voegele | A61F 15/005 401/132 |
| 2003/0068189 | A1 * | 4/2003 | Tsaur | B65D 81/3283 401/133 |
| 2003/0099501 | A1 * | 5/2003 | Fukushima | B43K 7/08 401/206 |
| 2005/0147455 | A1 * | 7/2005 | Muhr-Sweeney | B08B 1/00 401/23 |
| 2005/0186013 | A1 * | 8/2005 | Oike | B43K 5/005 401/23 |
| 2005/0279350 | A1 * | 12/2005 | Rasor et al. | 128/200.14 |
| 2007/0147946 | A1 | 6/2007 | Cybulski et al. | |
| 2010/0010473 | A1 * | 1/2010 | D'Alessio et al. | 604/520 |

OTHER PUBLICATIONS

Written Opinion of the International Search Authority of PCT/IL2011/000657, dated Feb. 21, 2012.

International Preliminary Report on Patentability of PCT/IL2011/000657, dated Feb. 12, 2013.

* cited by examiner

SECTION C-C

SECTION D-D

ACTIVE AGENT DELIVERY DEVICE

CROSS-REFERENCE TO RELATED APPLICATIONS

This application is a national phase entry under 35 U.S.C. 371(c) of International (PCT) Application No. PCT/IL2011/000598 (filed 25 Jul. 2011), which claims priority to Israel Patent Application No. 207208 (filed 25 Jul. 2010), both of which are hereby incorporated by reference in their entirety.

FIELD OF THE INVENTION

The present invention generally relates to active agent delivery devices, and more specifically, to an active agent delivery device useful for treatment of tissue lesions.

BACKGROUND OF THE INVENTION

A skin lesion is a superficial growth or patch of the skin that does not resemble the area surrounding it. Skin lesions can be grouped into two categories: primary and secondary. Primary skin lesions are variations in color or texture that may be present at birth, such as moles or birthmarks, or that may be acquired during a person's lifetime, such as those associated with infectious diseases (e.g. warts or acne), allergic reactions (e.g. hives or contact dermatitis), or environmental agents (e.g. sunburn, pressure, or temperature extremes). Secondary skin lesions are those changes in the skin that result from primary skin lesions, either as a natural progression or as a result of a person manipulating (e.g. scratching or picking at) a primary lesion.

Although there are certain methods and techniques for application of skin medications and for treatment of skin lesions, the main effort has been given so far to the development of transdermal drug delivery systems in the form of patches, designed to deliver drugs into the sub-epidermal capillary blood vessel network, to achieve a systemic effect. There is still a long felt need to develop an easy to handle (e.g., pen-like) drug delivery device which will enable to provide a controlled quick and precise dosage, and precise pressure and depth of a topical drug delivery to a skin lesion (intra-epidermally or intradermally) or any other purposes, to obtain optimal clinical results.

SUMMARY OF THE INVENTION

It is one object of the present invention to disclose, according to certain embodiments, a device for delivering an active agent to a tissue. The device comprises:
a. a housing including a reservoir for containing the active agent;
b. a delivery tip being in fluid communication with the reservoir; and,
c. a delivery mechanism capable of delivering a predetermined amount of the active agent and releasing the same upon contact between the delivery tip and the tissue.

It is another object of the present invention to disclose, according to certain embodiments, a device as defined above, wherein the delivery tip is made of substantially porous and substantially rigid material adapted to delay passage of the predetermined amount of the active agent through the delivery tip. The delivery tip is adapted to: (i) absorb at least part of the predetermined amount of the active agent; and (ii) discharge at least part of the predetermined amount of the active agent upon a contact of the delivery tip with the tissue.

It is another object of the present invention to disclose, according to certain embodiments, the device as defined above, wherein the delivery tip is made of a material selected from the group consisting of: wood, sponge/foam, felt, nylon, PTFE, Teflon®, PVDF, fluoropolymers, thermoplastic, thermoset and any combination thereof.

It is another object of the present invention to disclose, according to certain embodiments, the device as defined above, wherein the active agent delivery mechanism comprises a plunger.

It is another object of the present invention to disclose, according to certain embodiments, the device as defined above, wherein said plunger is adapted to actuate pushing forces on the active agent, the pushing forces are adapted to force the predetermined amount of the active agent to be delivered to the delivery tip.

It is another object of the present invention to disclose, according to certain embodiments, the device as defined above, wherein the plunger is adapted to actuate the pushing forces on the active agent via a first piston located between the plunger and the active agent.

It is another object of the present invention to disclose, according to certain embodiments, the device as defined above, further comprising a second piston located within the reservoir between the active agent and the delivery tip, the second piston adapted to control the passage of the active agent to the delivery tip.

It is another object of the present invention to disclose, according to certain embodiments, the device as defined above, wherein the second piston is adapted to be responsive to the pushing forces, the second piston is movable within the reservoir to provide a bypass to the active agent within the reservoir.

It is another object of the present invention to disclose, according to certain embodiments, the device as defined above, wherein the delivery tip is adapted to be in fluid communication with the reservoir though a channel.

It is another object of the present invention to disclose, according to certain embodiments, the device as defined above, wherein the plunger is located between the delivery tip and the reservoir.

It is another object of the present invention to disclose, according to certain embodiments, the device as defined above, wherein the channel extends within the plunger.

It is another object of the present invention to disclose, according to certain embodiments, the device as defined above, wherein the channel is a needle.

It is another object of the present invention to disclose, according to certain embodiments, the device as defined above, wherein the active agent delivery mechanism is further adapted to control the passage of the active agent from the reservoir and to the delivery tip.

It is another object of the present invention to disclose, according to certain embodiments, the device as defined above, wherein the active agent delivery mechanism comprises a knob adapted to control the operation of the active agent delivery mechanism.

It is another object of the present invention to disclose, according to certain embodiments, the device as defined above, further comprising a chip located at the second end of the housing, the chip is adapted to be used for spreading the active agent on the tissue following the delivery of the active agent to the tissue via the delivery tip.

It is another object of the present invention to disclose, according to certain embodiments, the device as defined above, wherein the chip is made of a material selected from the group consisting of: wood, sponge/foam, felt, nylon, PTFE, Teflon®, PVDF, fluoropolymers, thermoplastic, thermoset and any combination thereof.

It is another object of the present invention to disclose, according to certain embodiments, the device as defined above, further comprising an inspection window for providing information regarding the amount of the active agent within the reservoir.

It is another object of the present invention to disclose, according to certain embodiments, the device as defined above, wherein the inspection window is adapted to provide indication regarding the fluid communication of the reservoir with the delivery tip.

It is another object of the present invention to disclose, according to certain embodiments, the device as defined above, wherein the applicator is adapted to incorporate a cap, the cap is adapted to prevent delivery of the active agent out of the device.

It is another object of the present invention to disclose, according to certain embodiments, the device as defined above, wherein the active agent comprises substances selected from the group consisting of: trichloroacetic acid, formic acid, and any combination thereof.

It is another object of the present invention to disclose, according to certain embodiments, the device as defined above, wherein said active agent delivery mechanism comprises an elastomeric stopper adapted to be located between said reservoir and said delivery tip, such that when said elastomeric stopper is punctured via a spike, a fluid communication is established between said reservoir and said delivery tip.

It is another object of the present invention to disclose, according to certain embodiments, the device as defined above, wherein the device is adapted for treatment of tissue lesions.

It is another object of the present invention to disclose, according to certain embodiments, the device as defined above, wherein the container is a single use part.

It is another object of the present invention to disclose, according to certain embodiments, the device as defined above, wherein the device is a single use part.

It is another object of the present invention to disclose, according to certain embodiments, the device as defined above, wherein the housing is a multi use part.

It is another object of the present invention to disclose, according to certain embodiments, an active agent delivery device adapted to be applied to a tissue of a subject. The device comprises:
a. a housing with a first end and a second end, the housing comprising a reservoir for storing an active agent;
b. an applicator located at the first end of the housing, the applicator comprising a delivery tip adapted to be in fluid communication with the reservoir;
c. a first piston adapted to compress the fluid within the reservoir;
d. a plunger located within the housing between the first piston and the delivery tip and connected to the applicator, the plunger adapted to push the first piston towards the reservoir, so that pushing forces are actuated on the active agent, and a predetermined amount of the active agent is delivered to the delivery tip;
e. a needle adapted to fluidly connect the delivery tip with the reservoir, the needle extending within the plunger, the needle having a needle delivery tip protruding out of the plunger, the needle delivery tip adapted to pierce the first piston when a contact between the plunger and the first piston being established, so as to provide a fluid communication between the delivery tip and the reservoir.

It is within the scope of the present invention that the delivery tip is a made of substantially porous and substantially rigid material adapted to delay a passage of the predetermined amount of the active agent through the delivery tip; further wherein the delivery tip is adapted to: (i) absorb at least part of the predetermined amount of the active agent; and (ii) discharge at least part of the predetermined amount of the active agent upon a contact of the delivery tip with the tissue.

It is another object of the present invention to disclose, according to certain embodiments, an active agent delivery device as defined above, wherein the delivery tip is made of a material selected from the group consisting of: wood, sponge/foam, felt, nylon, PTFE, Teflon®, PVDF, fluoropolymers, thermoplastic, thermoset and any combination thereof.

It is another object of the present invention to disclose, according to certain embodiments, an active agent delivery device as defined above, wherein when the needle is located out of the first piston, a fluid communication between the reservoir and the delivery tip is absent, such that a delivery of the active agent to the delivery tip is prevented.

It is another object of the present invention to disclose, according to certain embodiments, an active agent delivery device as defined above, wherein the applicator is adapted to be pushed towards the direction of the second end so as to puncture the first piston via the needle and to push the first piston towards the reservoir, such that a predetermined amount of the active agent is delivered to the delivery tip.

It is another object of the present invention to disclose, according to certain embodiments, an active agent delivery device as defined above, wherein the applicator is adapted to be pulled towards the direction of the first end so as to pull the needle out of the first piston, such that the fluid communication between the delivery tip and the reservoir is interrupted.

It is another object of the present invention to disclose, according to certain embodiments, an active agent delivery device as defined above, wherein the first end is adapted to be rotated in a stepped manner with respect to the second end of the housing so as to puncture the first piston via the needle and to push the first piston towards the reservoir, such that a predetermined amount of the active agent is delivered to the delivery tip.

It is another object of the present invention to disclose, according to certain embodiments, an active agent delivery device as defined above, wherein the first end is adapted to be rotated in a stepped manner with respect to the second end of the housing so as to pull the needle out of the first piston, such that the fluid communication between the delivery tip and the reservoir is interrupted.

It is another object of the present invention to disclose, according to certain embodiments, an active agent delivery device as defined above, further comprising a chip located at the second end of the housing, the chip is adapted to be used for spreading the active agent on the tissue following the delivery of the active agent to the tissue via the delivery tip.

It is another object of the present invention to disclose, according to certain embodiments, an active agent delivery device as defined above, wherein the chip is made of a material selected from the group consisting of: wood, sponge/foam, felt, nylon, PTFE, Teflon®, PVDF, fluoropolymers, thermoplastic, thermoset and any combination thereof.

It is another object of the present invention to disclose, according to certain embodiments, an active agent delivery device as defined above, further comprising an inspection window for providing information regarding the amount of the active agent within the reservoir.

It is another object of the present invention to disclose, according to certain embodiments, an active agent delivery device as defined above, wherein the inspection window is adapted to provide indication regarding the position of the needle with respect to the first piston so as to indicate the existence of the fluid communication between the reservoir with the delivery tip.

It is another object of the present invention to disclose, according to certain embodiments, an active agent delivery device as defined above, wherein the active agent comprises substances selected from the group consisting of: trichloroacetic acid, formic acid, and any combination thereof.

It is another object of the present invention to disclose, according to certain embodiments, an active agent delivery device as defined above, wherein the device is adapted for treating tissue lesions.

It is another object of the present invention to disclose, according to certain embodiments, a method for delivering an active agent to be applied to a tissue of a subject. The method comprises steps of:
a. providing an active agent delivery device adapted to be applied to a tissue of a subject, comprising: (i) a housing with a first end and a second end, the housing comprising a reservoir for storing an active agent; (ii) an applicator located at the first end of the housing, the applicator is adapted to incorporate a delivery tip adapted to be in fluid communication with the reservoir; and, (iii) an active agent delivery mechanism mechanically connected to the reservoir; the delivery tip being a made of substantially porous and substantially rigid material adapted to delay a passage of the predetermined amount of the active agent through the delivery tip;
b. connecting the delivery tip to the applicator;
c. delivering a predetermined amount of the active agent to the delivery tip via the active agent delivery mechanism;
d. absorbing at least part of the predetermined amount of the active agent in the delivery tip; and,
e. discharging at least part of the predetermined amount of the active agent upon a contact of the delivery tip with the tissue, thereby treating the tissue of the subject.

It is another object of the present invention to disclose, according to certain embodiments, a method for delivering an active agent as defined above, further comprising a step of selecting the material of the delivery tip from the group consisting of: wood, sponge/foam, felt, nylon, PTFE, Teflon®, PVDF, fluoropolymers, thermoplastic, thermoset and any combination thereof.

It is another object of the present invention to disclose, according to certain embodiments, a method for delivering an active agent as defined above, wherein the active agent delivery mechanism comprises a plunger.

It is another object of the present invention to disclose, according to certain embodiments, a method for delivering an active agent as defined above, wherein the step (c) of delivering a predetermined amount of the active agent to the delivery tip further comprising step of actuating pushing forces on the active agent via the plunger.

It is another object of the present invention to disclose, according to certain embodiments, a method for delivering an active agent as defined above, further comprising steps of: providing the device with a first piston located between the plunger and the active agent, and actuating pushing forces on the active agent via the plunger and the piston.

It is another object of the present invention to disclose, according to certain embodiments, a method for delivering an active agent as defined above, further comprising steps of: providing the device with a second piston located within the reservoir between the active agent and the delivery tip, and controlling passage of the active agent to the delivery tip via the second piston.

It is another object of the present invention to disclose, according to certain embodiments, a method for delivering an active agent as defined above, further comprising step of applying the pushing forces on the second piston, thereby moving the second piston within the reservoir to provide a bypass to the active agent.

It is another object of the present invention to disclose, according to certain embodiments, a method for delivering an active agent as defined above, wherein the delivery tip is adapted to be in fluid communication with the reservoir though a channel.

It is another object of the present invention to disclose, according to certain embodiments, a method for delivering an active agent as defined above, wherein the plunger is located between the delivery tip and the reservoir.

It is another object of the present invention to disclose, according to certain embodiments, a method for delivering an active agent as defined above, wherein the channel is extending within the plunger.

It is another object of the present invention to disclose, according to certain embodiments, a method for delivering an active agent as defined above, wherein the channel is a needle.

It is another object of the present invention to disclose, according to certain embodiments, a method for delivering an active agent as defined above, further comprising step of controlling the passage of the active agent from the reservoir and to the delivery tip via the active agent delivery mechanism.

It is another object of the present invention to disclose, according to certain embodiments, a method for delivering an active agent as defined above, further comprising steps of: providing the active agent delivery mechanism with a knob, and controlling the operation of the active agent delivery mechanism via the knob.

It is another object of the present invention to disclose, according to certain embodiments, a method for delivering an active agent as defined above, further comprising step of providing the device with a chip located at the second end of the housing, the chip being adapted to be used for spreading the active agent on the tissue following the delivery of the active agent to the tissue via the delivery tip.

It is another object of the present invention to disclose, according to certain embodiments, a method for delivering an active agent as defined above, further comprising a step of selecting the material of the chip from the group consisting of: wood, sponge/foam, felt, nylon, PTFE, Teflon®, PVDF, fluoropolymers, thermoplastic, thermoset and any combination thereof.

It is another object of the present invention to disclose, according to certain embodiments, a method for delivering an active agent as defined above, further comprising a step of providing information regarding the amount of the active agent within the reservoir via an inspection window.

It is another object of the present invention to disclose, according to certain embodiments, a method for delivering an active agent as defined above, further comprising a step of providing indication regarding the fluid communication of the reservoir with the delivery tip via the inspection window.

It is another object of the present invention to disclose, according to certain embodiments, a method for delivering an active agent as defined above, further comprising step of connecting a cap to the applicator in stead of the delivery tip, thereby preventing delivery of the active agent out of the device.

It is another object of the present invention to disclose, according to certain embodiments, a method for delivering an active agent as defined above, wherein the active agent comprises substances selected from the group consisting of: trichloroacetic acid, formic acid, and any combination thereof.

It is another object of the present invention to disclose, according to certain embodiments, a method for delivering an active agent as defined above, wherein the device is adapted for treating tissue lesions.

It is another object of the present invention to disclose, according to certain embodiments, a method for delivering an active agent as defined above, further comprising steps of: providing said active agent delivery mechanism with an elastomeric stopper adapted to be located between said reservoir and said delivery tip; and, puncturing said elastomeric stopper via a spike, thereby establishing a fluid communication between said reservoir and said delivery tip.

It is another object of the present invention to disclose, according to certain embodiments, an active agent for treating tissue lesions. The active agent comprises: trichloroacetic acid; and, formic acid, wherein the preparation is adapted for administration by an active agent delivery device adapted to be applied to a tissue of a subject, comprising: (i) a housing with a first end and a second end, the housing comprising a reservoir for storing an active agent; (ii) an applicator located at the first end of the housing, the applicator is adapted to incorporate a delivery tip adapted to be in fluid communication with the reservoir; and, (iii) an active agent delivery mechanism mechanically connected to the reservoir, the active agent delivery mechanism adapted to deliver a predetermined amount of the active agent to the delivery tip; the delivery tip being a made of substantially porous and substantially rigid material adapted to delay passage of the predetermined amount of the active agent through the delivery tip; the delivery tip adapted to: (i) absorb at least part of the predetermined amount of the active agent; and (ii) discharge at least part of the predetermined amount of the active agent upon a contact of the delivery tip with the tissue.

BRIEF DESCRIPTION OF THE FIGURES

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

Figure 1:
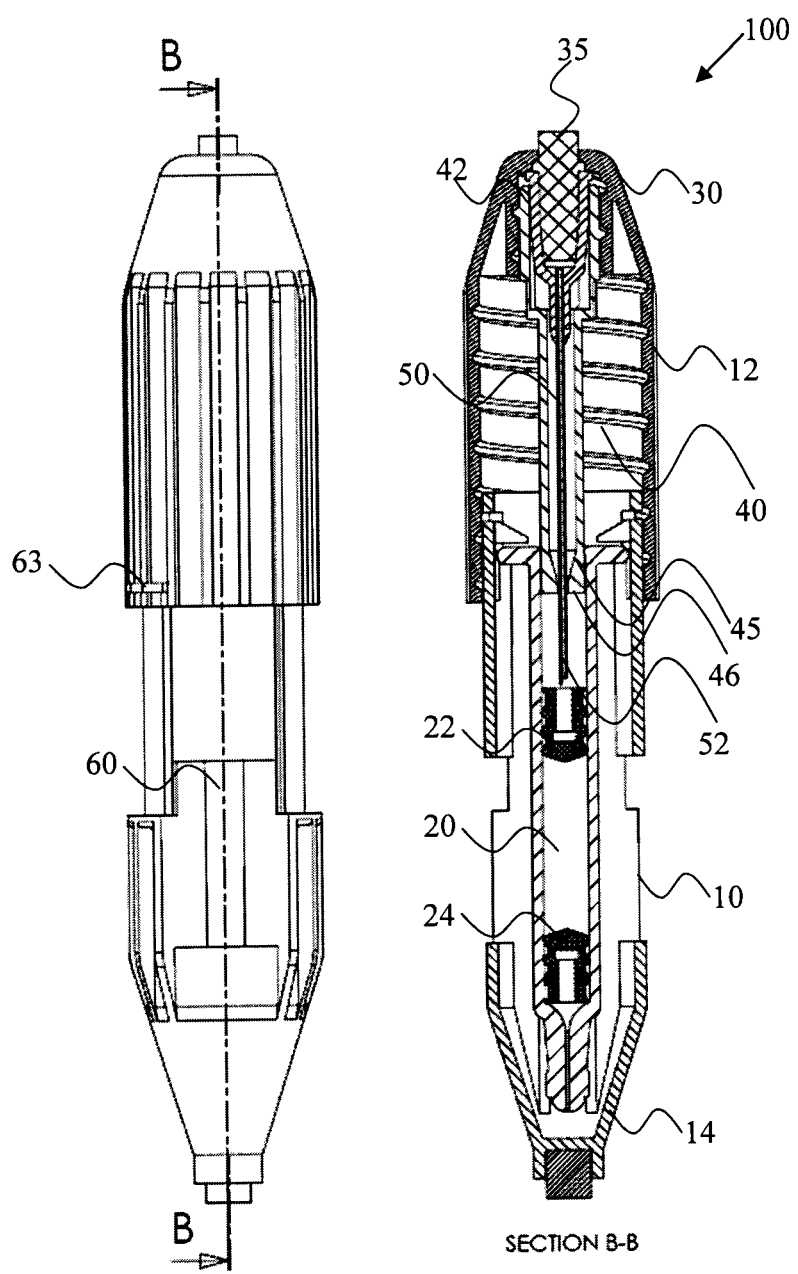
FIG. 1 is an illustration of a first embodiment of the present invention in a position which the device 100 is before usage.

The drawings together with the description make apparent to those skilled in the art how the invention may be embodied in practice.

DETAILED DESCRIPTION OF THE PREFERRED EMBODIMENTS

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The present invention is related to the field of active agent delivery devices which may be applied to a tissue of a subject. The device of the present invention may be used, for example, for treatments of tissue lesions. According to different embodiments of the present invention, the active agent is delivered to the present invention by spreading the active agent on the subject's tissue.

The present invention discloses a device for delivering an active agent to a tissue. The device comprises: a housing including a reservoir for containing the active agent; a delivery tip which is in fluid communication with the reservoir; and, a delivery mechanism capable of delivering a predetermined amount of the active agent and releasing the same upon contact between the delivery tip and the tissue.

The term 'active agent' refers hereinafter to any known in the art pharmaceutical composition or drug which may be used for treating skin disorders or any other transdermal/intra-epidermal/intradermal drug administration.

The term 'active agent delivery mechanism' refers hereinafter to a mechanism which is adapted to deliver an active agent from one location to another location. For example, the active agent delivery mechanism may be a plunger.

The term 'predetermined' refers hereinafter to any amount of a substance, a force, or any other measurable physical entity. This can also be a certain amount of a substance, a force or any other physical entity. This certain amount may be not limited to a specific amount of a substance, a force or any other physical entity.

Reference is now made to FIGS. 1-5 which schematically illustrate an active agent delivery device 100 according to a specific embodiment of the present invention. According to this embodiment, active agent delivery device 100 comprises the following components:

a. A housing 10 with a first end 12 and a second end 14. Housing 14 may comprise a reservoir 20 which is configured for storing an active agent.

b. An applicator 30 located at first end 12 of housing 10. The applicator 30 is adapted to incorporate a delivery tip 35. The delivery tip 35 is adapted to be in fluid communication with reservoir 20.

c. An active agent delivery mechanism 40 mechanically connected to reservoir 20. The active agent delivery mechanism 40 is adapted to deliver a predetermined amount of active agent (not shown) to delivery tip 35.

According to certain embodiments of the present invention, delivery tip 35 is a made of substantially porous and substantially rigid material adapted to delay passage of the predetermined amount of the active agent through delivery tip 35. When the predetermined amount of the active agent delivered to delivery tip 35, the delivery tip is adapted to: (i) absorb at least part of the predetermined amount of the active agent; and (ii) discharge at least part of the predetermined amount of the active agent upon a contact of delivery tip 35 with the subject's tissue. The delivery of the active agent may be performed when the device is in the primed position (a position in which the active agent is ready to be delivered through the tip).

According to certain embodiments, the discharge of the active agent through delivery tip 35 may occur in the air, following the contact of the delivery tip 35 with the subject's tissue.

According to different embodiments of the present invention, the active agent delivery mechanism is adapted to control the passage of active agent from reservoir and to delivery tip. As part of the control, the active agent delivery mechanism may establish or prevent fluid communication between delivery tip 35 and reservoir 20.

According to different embodiments of the present invention, the active agent delivery device may be a single-use device, or may comprise single use elements (e.g., a container or cartridge with an active agent).

According to other embodiments, the active agent delivery device may be used as a multi use device, or may comprise multi use elements.

According to different embodiments of the present invention, the active agent delivery mechanism may comprise a knob adapted to control the operation of the active agent delivery mechanism.

According to the embodiment of FIGS. 1-5, the knob may be a rotational mechanism by which first end 12 is rotated with respect to second end 14. By rotating first end 12 with respect to second end 14, device 100 is actuated, so as to deliver the active agent to delivery tip 35.

According to different embodiments of the present invention, delivery tip 35 may be made of a material such as but not limited to be: wood, sponge, foam, felt, nylon, PTFE, Teflon®, PVDF, fluoropolymers, thermoplastic, thermoset, and any combination thereof. According to other embodiments, delivery tip 35 may be made of any other material which is able to provide the characteristics mentioned about related to the absorbance and the delivery of the active agent.

Referring to FIG. 1, delivery tip 35 is placed in needle hub 42. Needle 50 is adapted to create fluid communication between delivery tip 35 and reservoir 20.

According to this embodiment, active agent delivery mechanism 40 comprises a plunger 45 located between delivery tip 35 and reservoir 20. Plunger 45 is inserted over needle 50 such that the needle delivery tip 52 is protruding from the edge of plunger 45. Plunger 45 is screwed into first end 12 of housing 10, thereby securing delivery tip 35 to needle hub 42 and preventing leakages.

According to the specific embodiment of FIG. 1, reservoir 20 comprises a first piston 22 and a second piston 24. First piston 22 and second piston 24 are spaced apart creating in between a sealed chamber which may contain the active agent.

According to FIG. 1, reservoir 20 is inserted into the middle portion of housing 10, between the first and the second ends of housing 10. Reservoir 20 is locked to second end 14 of housing 10, such that axial movement of the same is prevented.

According to this embodiment, when needle 50 is located out of first piston 22, a fluid communication between reservoir 20 and delivery tip 35 is absent, such that a delivery of the active agent to delivery tip 35 is prevented. First end 12 may be rotated in a stepped manner with respect to second end 14 of housing 10 so as to puncture first piston 22 via needle 50 and to push first piston 22 towards the active agent in reservoir 20, such that a predetermined amount of the active agent is delivered to delivery tip 35.

According to other embodiments, first end 12 may be rotated in a stepped manner with respect to second end 14 of housing 10 so as to pull needle 50 out of first piston 22, such that the fluid communication between delivery tip 35 and reservoir 20 is interrupted.

Before operation, according to FIG. 1, needle delivery tip 52 does not pierce first piston 22, and plunger 45 is distanced from the dry surface of first piston 22. At this position, there is no fluid communication between reservoir 20 and delivery tip 35.

According to some embodiments, active agent delivery device 100 may comprise an inspection window 60 for providing information regarding the amount of active agent within reservoir 20, the location of needle delivery tip 52 (out of first piston 22, or within first piston 22).

Figure 2:
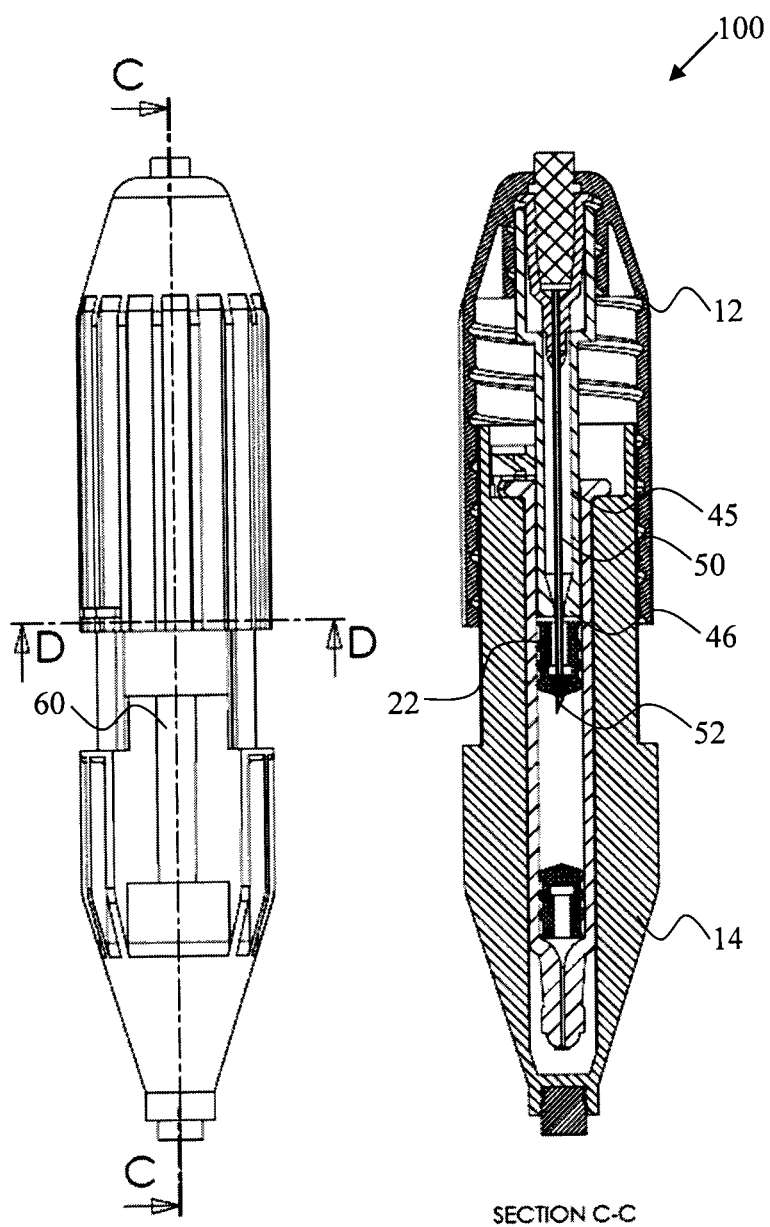
FIG. 2 is an illustration of a first embodiment of the present invention in a position in which the device 100 is ready to be used or is primed for use.

In preparation for operation, as illustrated in FIG. 2, first end 12 of housing 10 is rotated with respect to second end 14 in a clockwise direction. As a result of that, plunger 45 and needle 50 advance towards first piston 22, while needle delivery tip 52 starts to pierce first piston 22. The preparation for operation is finished once needle delivery tip 52 has fully penetrated first piston 22 and plunger edge 46 engages the dry face of first piston 22. Inspection window 60 enables view of needle delivery tip 52 after piercing. Since needle delivery tip 52 has pierced first piston 22, a fluid communication between reservoir 20 and delivery tip 35 is established.

Figure 3:
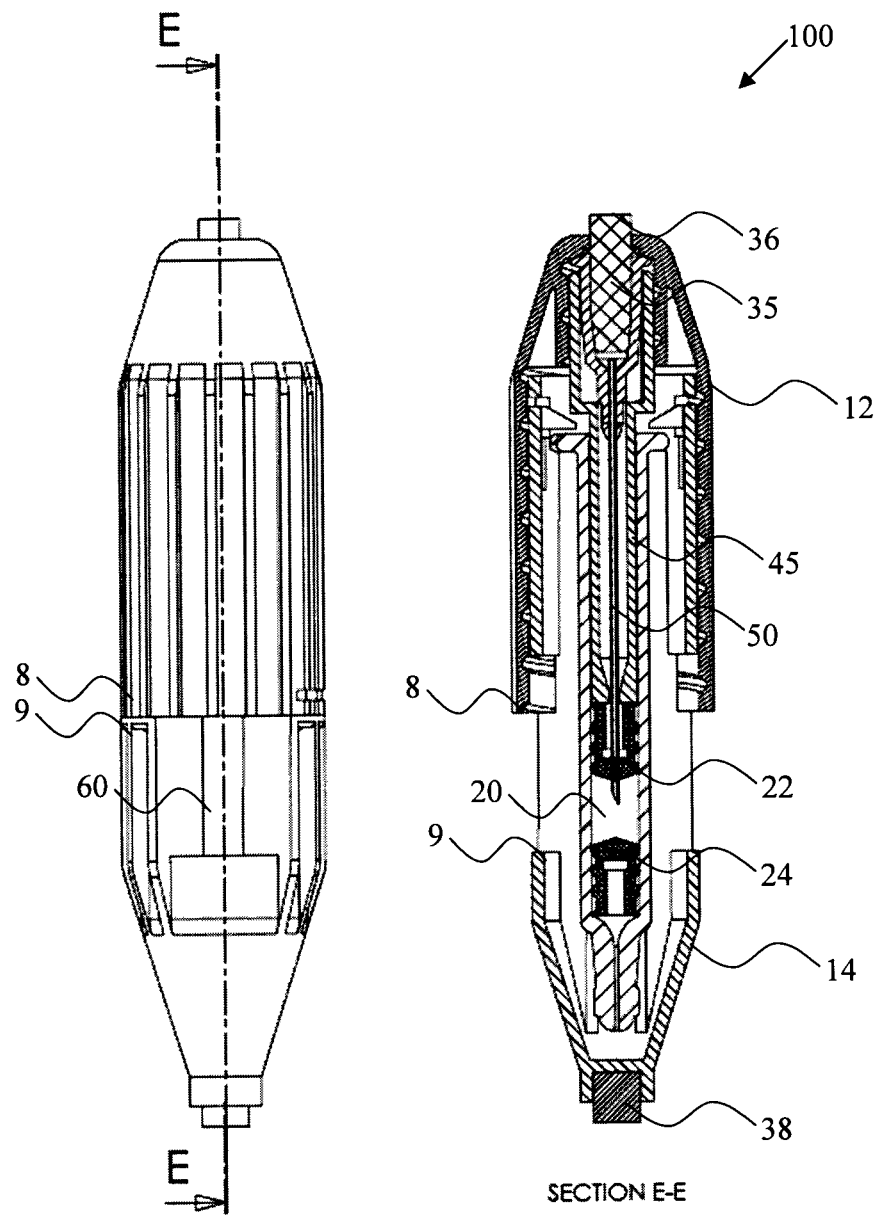
FIG. 3 is an illustration of a first embodiment of the present invention in a position in which the device 100 is used.
Figure 4:
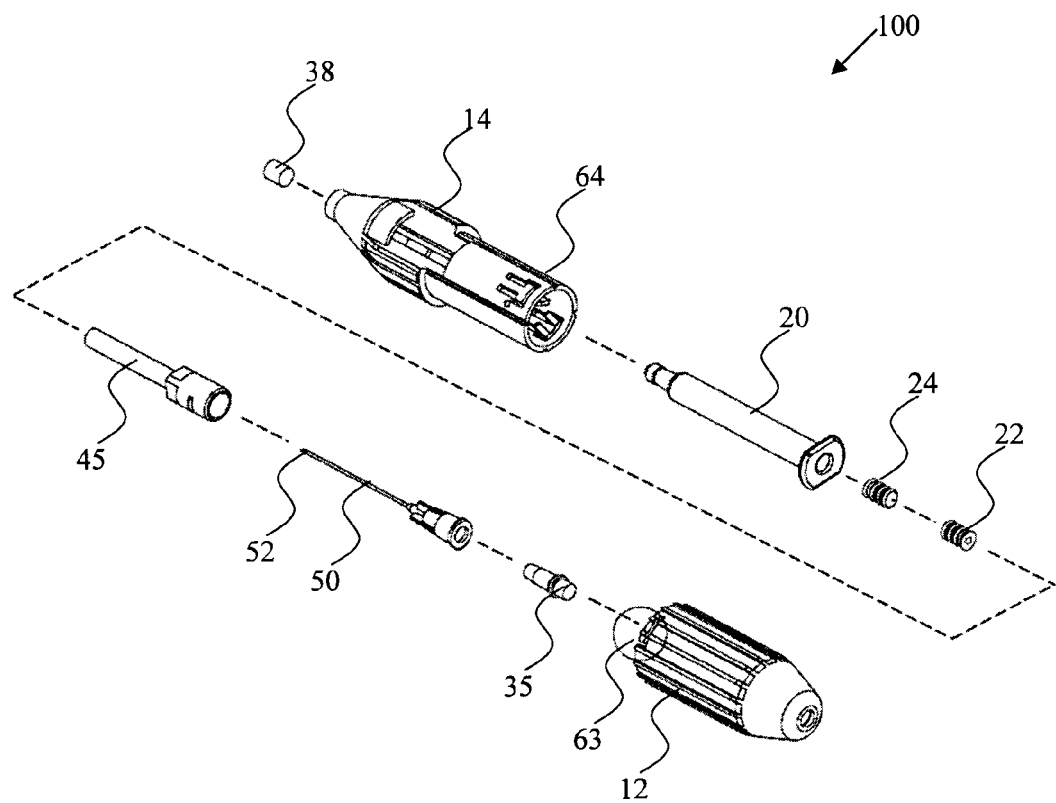
FIG. 4 is an illustration of a first embodiment of the present invention in which the elements of device 100 are presented in exploded view.
Figure 5:
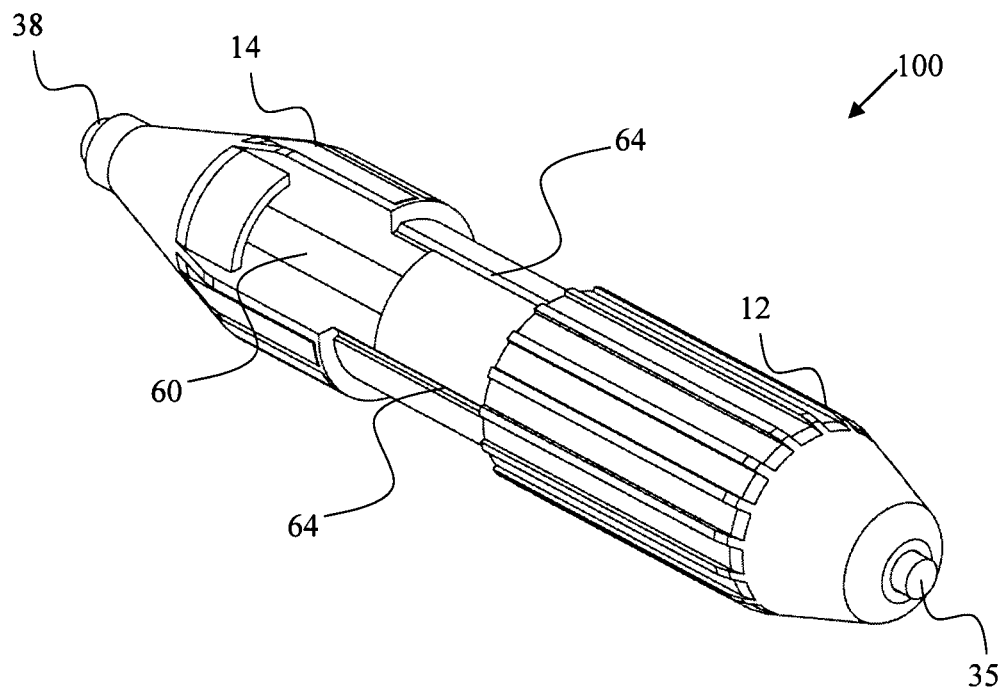
FIG. 5 is an illustration of a first embodiment of the present invention in which an isometric view of device 100 is presented.

In operation, as illustrated in FIG. 3, by further rotating first end 12 of housing 10 with respect to second end 14 in a clockwise direction, plunger 45 pushes first piston 22 towards second piston 24. The pushing of first piston 22 actuates pushing forces on the active agent within reservoir 20. The pushing forces are adapted to force the predetermined amount of the active agent to be delivered to delivery tip 35 via needle 50. As a result of that, delivery tip 35 absorbs at least part of the predetermined amount of the active agent, and is ready to deliver the same to the tissue of the subject. For delivering the active agent to the subject's tissue, wetting end 36 of delivery tip 35 is applied on the subject's tissue (by contact). This results with discharging the active agent on the subject's tissue while the user of device 100 holds the device by hand. In order to assist penetration of the active agent to the patient's tissue, pressure on the tissue may be applied either by using wetting end 36 of delivery tip 35, or by using chip 38. When delivery tip 35 dries, further rotation of first end 12 with respect to second end 14 will cause delivery tip 35 to absorb additional portion of the active agent, and to be saturated again.

According to different embodiments of the present invention, chip 38 may be made of a material selected from the group consisting of: wood, sponge/foam, felt, nylon, PTFE, Teflon®, PVDF, fluoropolymers, thermoplastic, thermoset and any combination thereof.

According to the embodiment of FIGS. 1-5, chip 38 may be located at second end 14 of housing 10.

According to different embodiments, chip 38 may be used for spreading the active agent on the subject's tissue following the delivery of the active agent to the tissue via delivery tip 35. Chip 38 may also be used for actuating a predetermined pressure on the tissue to force the penetration of the active agent.

Inspection window 60 may be used for viewing the advancement of first piston 22 and the remaining active agent in reservoir 20.

According to the specific embodiment of the present invention illustrated in FIGS. 1-5, each quarter rotation of first end 12 with respect to second end 14 of housing 10 may release a fixed amount of active agent which is distinguished by audible sound and sudden reduction in rotational friction force. A directional ratchet 63 may encounter a longitudinal slot 64 located in housing 10 every quarter of rotation and clicks inwards, Due to the shape of the directional ratchet 63 and longitudinal slot 64, the rotation of first end 12 with respect to second end 14 is enabled only in one direction.

According to some embodiments, when first piston 22 engages second piston 24, the reservoir 20 is exhausted. In this case, additional rotation of the first end 12 is prevented. Alternatively, as shown in FIG. 3, the delivery of the active agent may terminate when end 8 of first end 12 reaches end 9 of second end 14.

Figure 6:
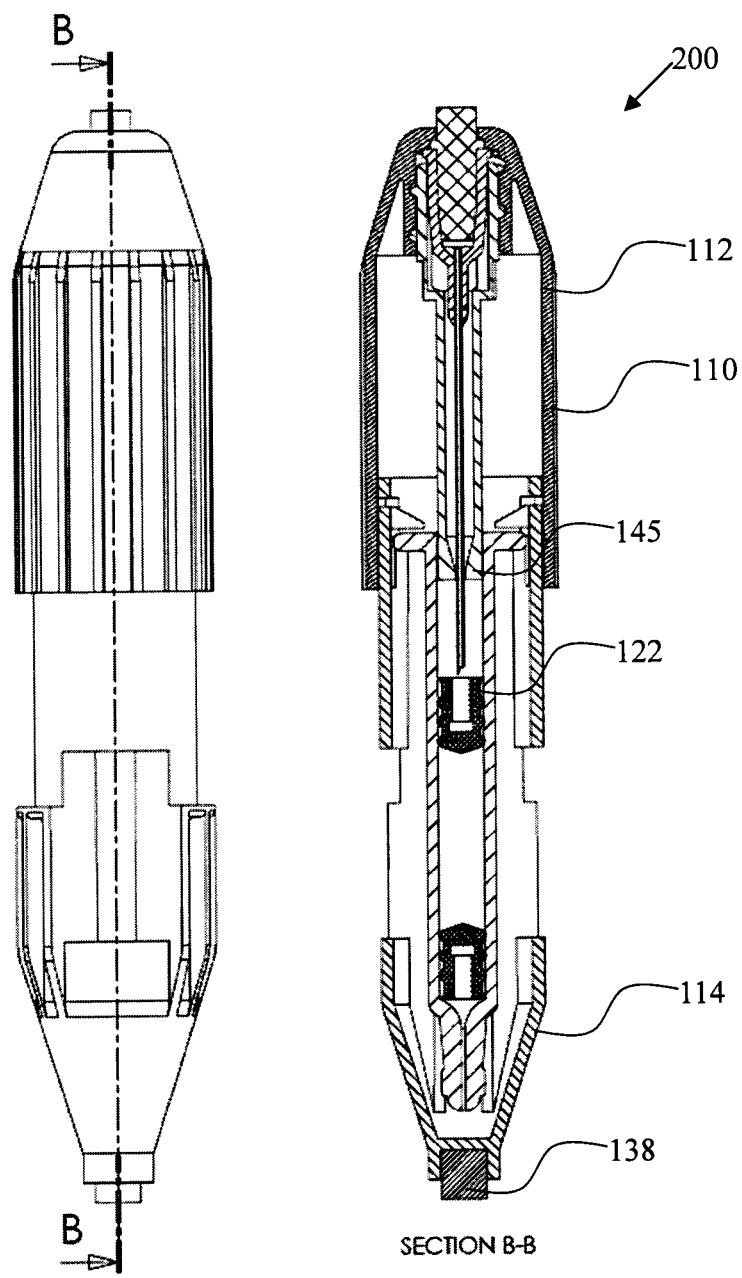
FIG. 6 is an illustration of a second embodiment of the present invention in a position which the device 200 is before usage.
Figure 7:
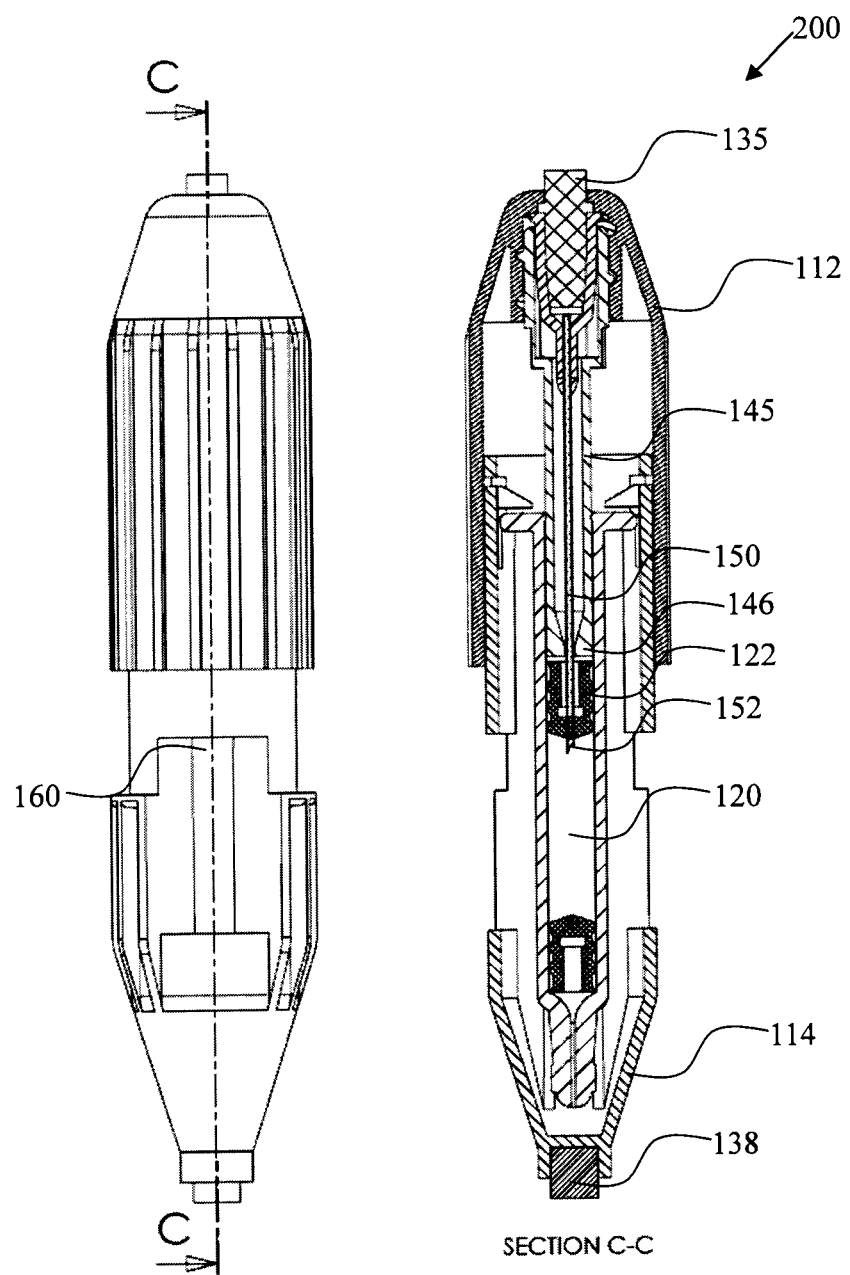
FIG. 7 is an illustration of a second embodiment of the present invention in a position in which the device 200 is ready to be used or is primed for use.
Figure 8:
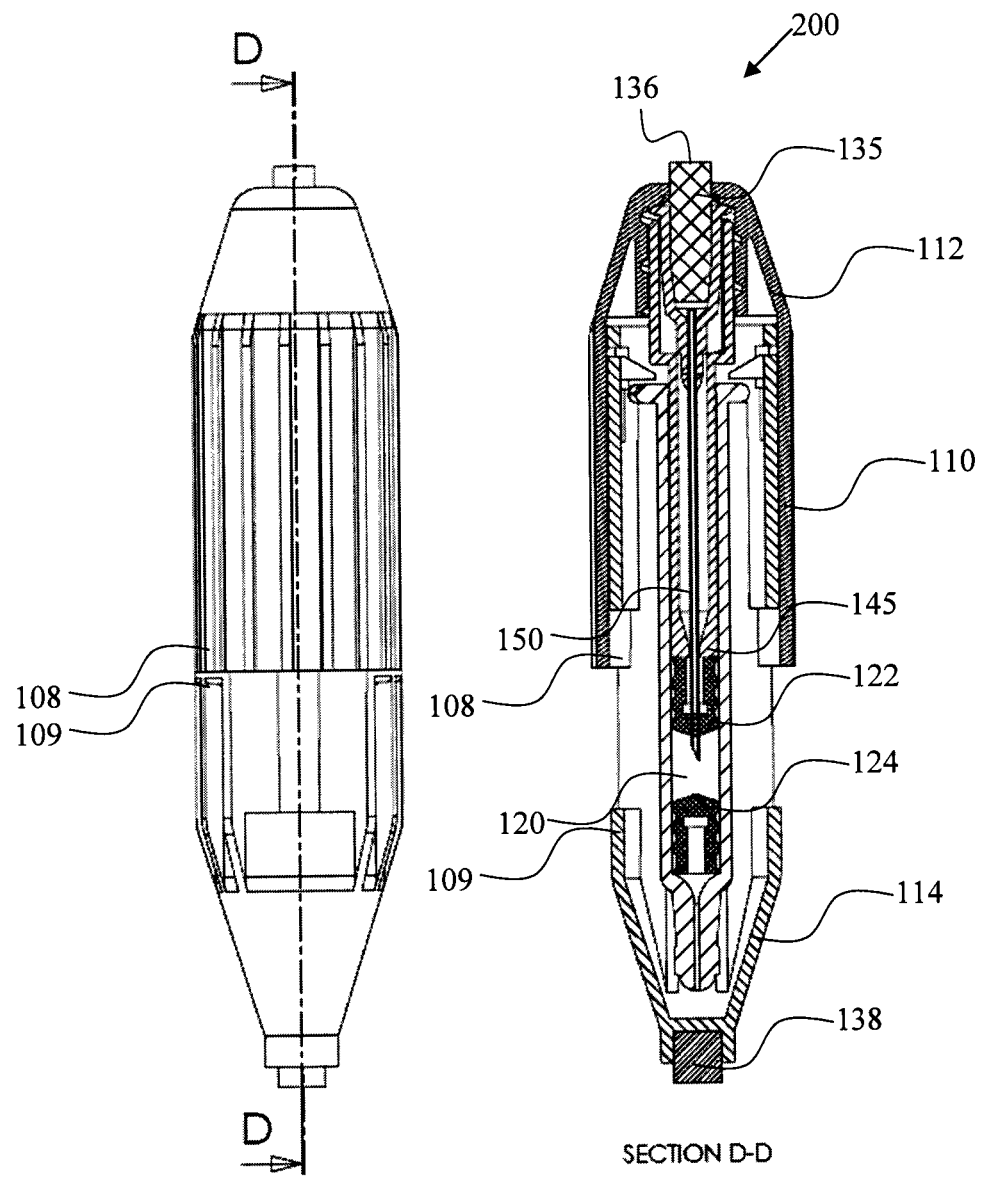
FIG. 8 is an illustration of a second embodiment of the present invention in a position in which the device 200 is used.

Reference is now made to FIGS. 6-8 which schematically illustrate another embodiment of the present invention. According to this embodiment, the main elements of active agent delivery device 200 are similar to the element of active agent delivery device 100. The main difference between the embodiment of device 200 and the embodiment of device 100 is the manner in which a plunger 145 is forced to move towards first piston 122. Differently from the stepped rotational manner in which this may be performed in the embodiment of device 100, in device 200 the first end 112 is pushed towards second end 114 of housing 110.

In preparation for operation, as illustrated in FIG. 7, first end 112 of housing 110 is pushed towards second end 114. As a result of that, plunger 145 and needle 150 advance towards first piston 122, while needle delivery tip 152 starts to pierce first piston 122. The preparation for operation is finished once needle delivery tip 152 has fully penetrated first piston 122 and plunger edge 146 engages the dry face of first piston 122. Inspection window 160 enables view of needle delivery tip 152 after piercing. Since needle delivery tip 152 has pierced first piston 122, a fluid communication between reservoir 120 and delivery tip 135 is established.

In operation, as illustrated in FIG. 8, by further pushing first end 112 of housing 110 towards second end 114, plunger 145 pushes first piston 122 towards second piston 124. The pushing of first piston 122 actuates pushing forces on the active agent within reservoir 120. The pushing forces are adapted to force the predetermined amount of the active agent to be delivered to delivery tip 135 via needle 150. As a result of that, delivery tip 135 absorbs at least part of the predetermined amount of the active agent, and is ready to deliver the same to the tissue of the subject. For delivering the active agent to the subject's tissue, wetting end 136 of delivery tip 135 is applied on the subject's tissue (by contact). This results with discharging the active agent on the subject's tissue while the user of device 200 holds the device by hand. In order to assist penetration of the active agent to the patient's tissue, pressure on the tissue may be applied either by using wetting end 136 of delivery tip 135, or by using chip 138. When delivery tip 135 dries, further pushing of first end 112 towards second end 114 will cause delivery tip 135 to absorb additional portion of the active agent, and to be saturated again.

According to some embodiments, when first piston 122 engages second piston 124, the reservoir 120 is exhausted. In this case, additional pushing of the first end 112 is prevented. Alternatively, as shown in FIG. 8, the delivery of the active agent may terminate when end 108 of first end 112 reaches end 109 of second end 114.

According to other embodiments, first end 112 of housing 110 may also be pulled towards the opposing direction of second end 114 so as to pull needle 150 out of first piston 122, such that the fluid communication between delivery tip 135 and reservoir 120 is interrupted.

Reference is now made to FIGS. 9-13, which schematically illustrate another embodiment of the present invention. According to these figures, active agent delivery device 300 comprises the following components:
a. A housing 210 with a first end 212 and a second end 214. Housing 210 comprises a reservoir 220 which is configured for storing an active agent.
b. An applicator 230 located at first end 212 of housing 210. The applicator 230 is adapted to incorporate a delivery tip 235. The delivery tip 235 is adapted to be in fluid communication with reservoir 220.
c. An active agent delivery mechanism 240 mechanically connected to reservoir 220. The active agent delivery mechanism 240 is adapted to deliver a predetermined amount of active agent (not shown) to delivery tip 235.

According to certain embodiments of the present invention, delivery tip 235 is a made of substantially porous and substantially rigid material adapted to delay passage of the predetermined amount of the active agent through delivery tip 235. When the predetermined amount of the active agent delivered to delivery tip 235, the delivery tip is adapted to: (i) absorb at least part of the predetermined amount of the active agent; and (ii) discharge at least part of the predetermined amount of the active agent upon a contact of delivery tip 235 with the subject's tissue.

According to different embodiments of the present invention, the active agent delivery mechanism is adapted to control the passage of active agent from reservoir and to delivery tip. As part of the control, active agent delivery mechanism may establish or prevent fluid communication between delivery tip 235 and reservoir 220.

Figure 9:
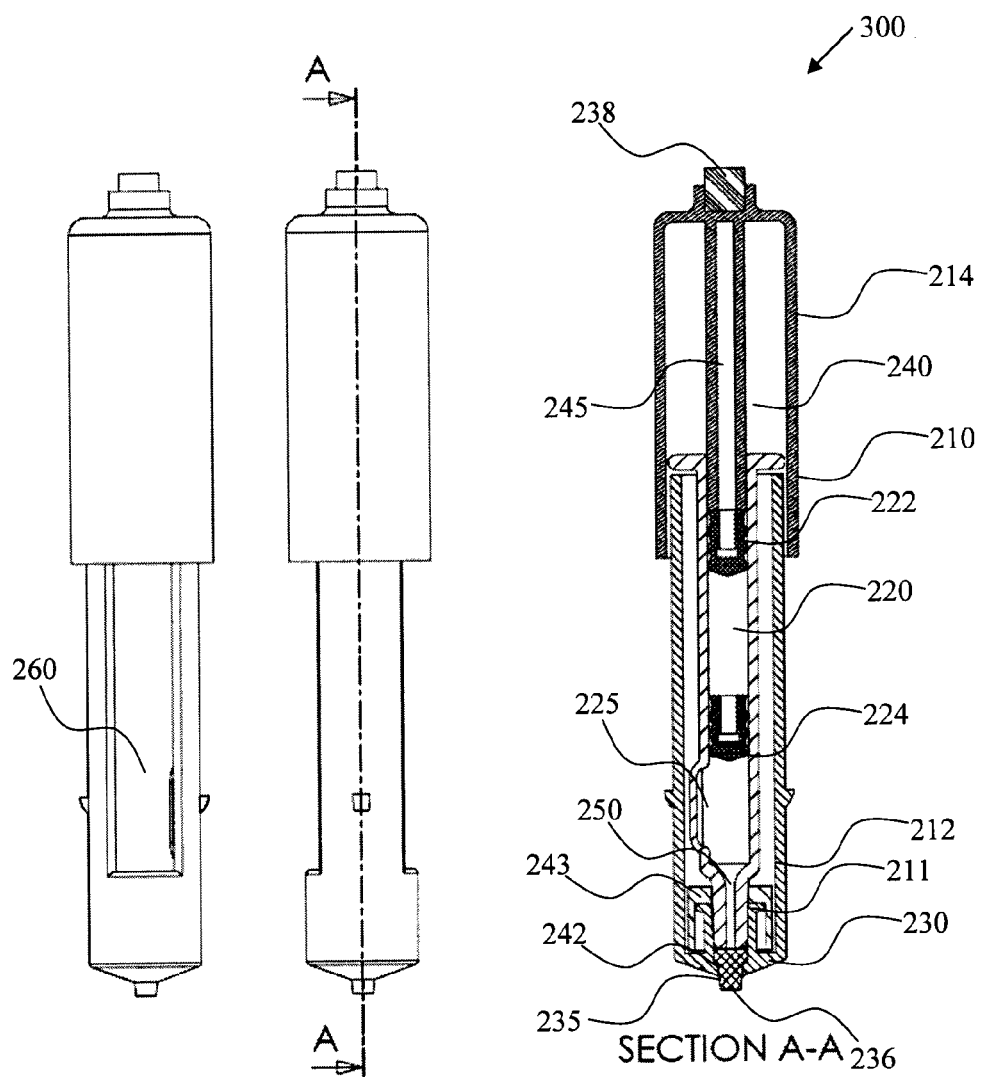
FIG. 9 is an illustration of a third embodiment of the present invention in a position which the device 300 is before usage.

Referring to FIG. 9, delivery tip 235 is placed in hub 242. Channel 250 is adapted to create fluid communication between delivery tip 235 and reservoir 220.

According to this embodiment, active agent delivery mechanism 240 comprises a plunger 245 located within and connected to second end 214. Plunger 245 may be screwed into second end 214 of housing 210.

According to the specific embodiment of FIG. 9, reservoir 220 comprises a first piston 222 and a second piston 224. Second piston 224 is adapted to control the passage of the active agent to delivery tip 235. First piston 222 and second piston 224 are spaced apart creating in between a sealed chamber which may contain the active agent. Second piston 224 is located above bypass 225. Male Luer Lock 243 may be assembled on reservoir 220. According to this embodiment first end 212 comprises female Luer Lock 211 to which male Luer Lock 243 may be screwed. Reservoir 220 may be assembled into female Luer Lock 211, thereby preventing axial movement of reservoir relative to first end 212.

As can be seen in FIG. 9, before operation, second piston 224 is distances from bypass 225. In this position, there is no fluid communication between the active agent and delivery tip 235. Inspection window 260 in housing 210 enables view of the active agent in reservoir 220.

Figure 10:
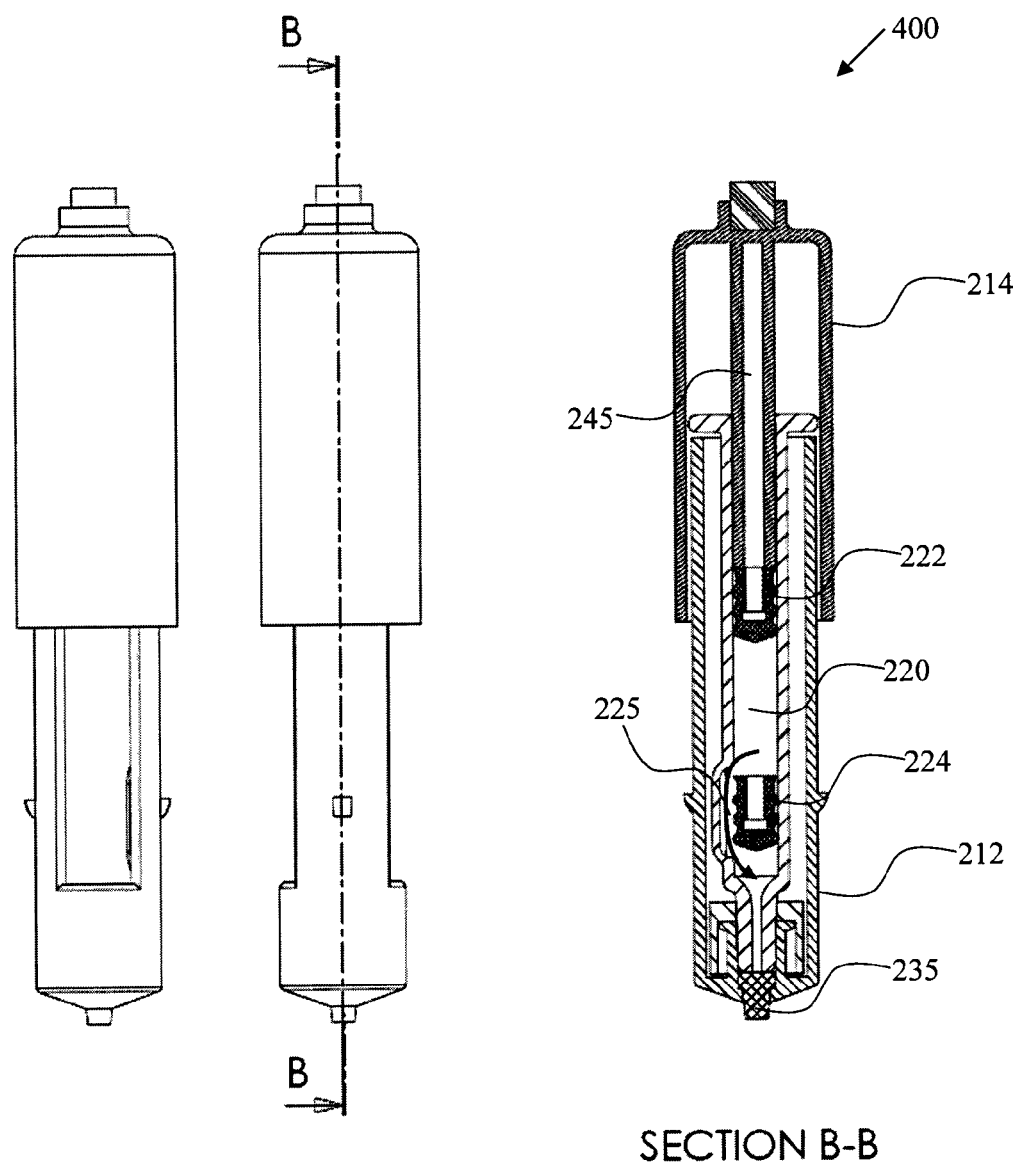
FIG. 10 is an illustration of a third embodiment of the present invention in a position in which the device 300 is ready to be used or is primed for use or used.

In operation, as illustrated in FIG. 10, by pushing second end 214 of housing 210 towards first end 212, plunger 245 pushes first piston 222 towards second piston 224. The pushing of first piston 222 actuates pushing forces on the active agent within reservoir 220. The pushing forces are adapted to force second piston 224 to move towards the direction of delivery tip 235. Once second piston 224 passed bypass 225, a fluid communication between reservoir 220 and delivery tip 235 is established. By further movement of second end 214 towards first end 212, first piston 222 is pushed towards second piston 224 forcing the active agent to bypass second piston 224 and flow towards delivery tip 235. As a result of that, delivery tip 235 absorbs at least part of the predetermined amount of the active agent, and is ready to deliver the same to the tissue of the subject by using wetting side 236 of delivery tip 235 which is saturated with the active agent. For delivering the active agent to the subject's tissue, wetting end 236 of delivery tip 235 is applied on the subject's tissue (by contact). This results with discharging the active agent on the subject's tissue while the user of device 300 holds the device by hand. In order to assist penetration of the active agent to the patient's tissue, pressure on the tissue may be applied either by using wetting end 236 of delivery tip 235, or by using chip 238. When delivery tip 235 dries, further pushing of second end 214 towards first end 212 will cause delivery tip 235 to absorb additional portion of the active agent, and to be saturated again.

Figure 11:
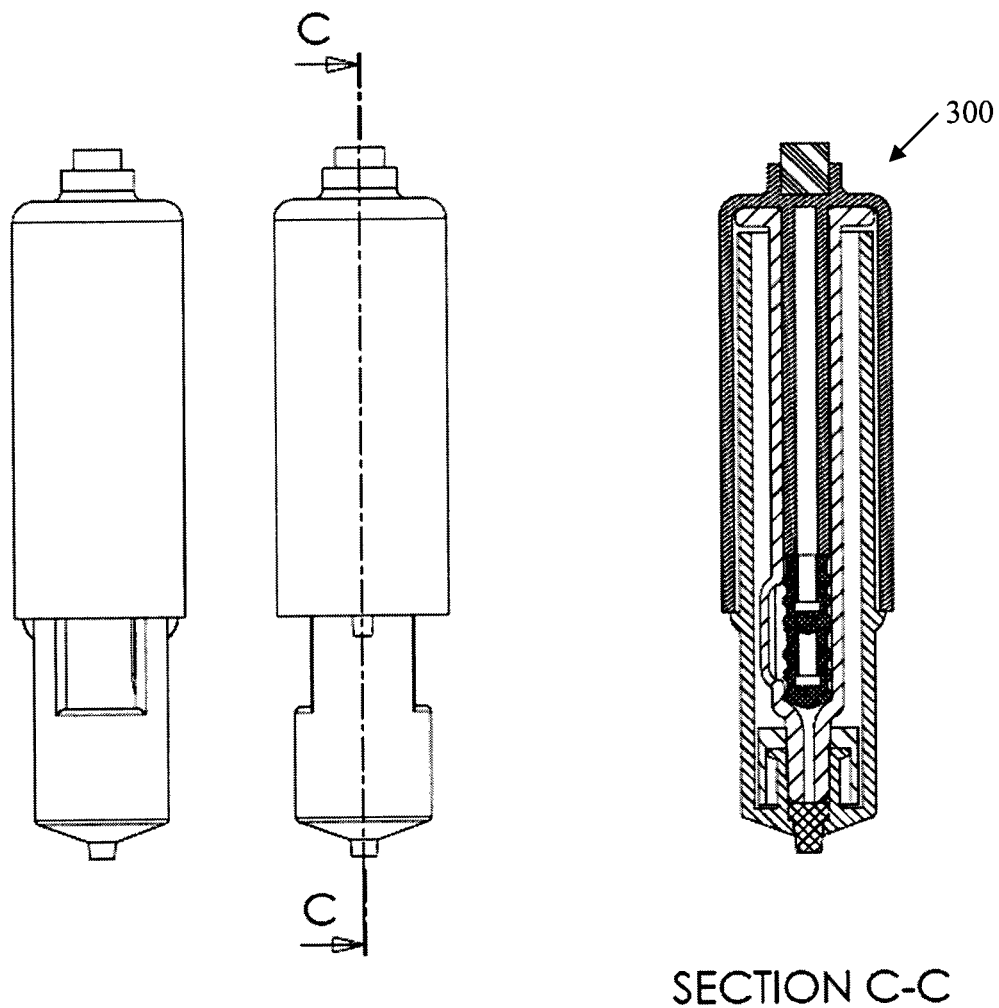
FIG. 11 is an illustration of a third embodiment of the present invention in a position in which the device 300 is used or its usage is terminated.
Figure 12:
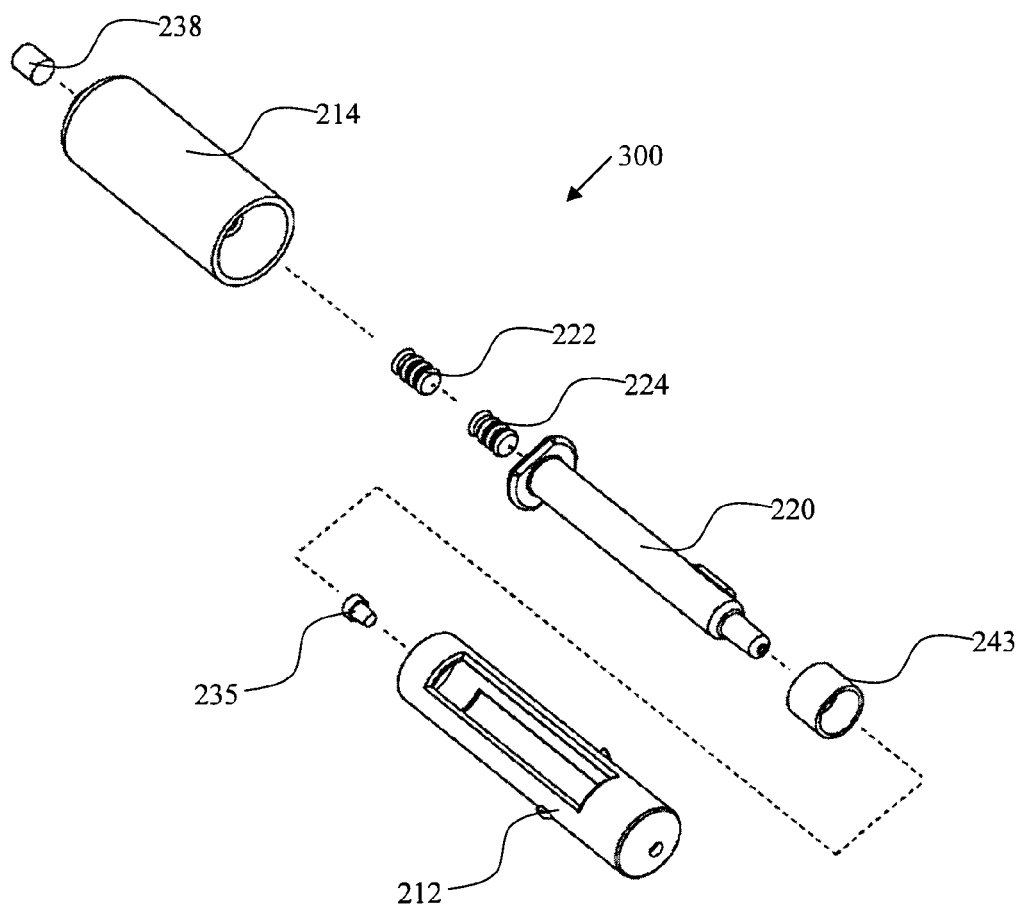
FIG. 12 is an illustration of a third embodiment of the present invention in which the elements of device 300 are presented in exploded view.
Figure 13:
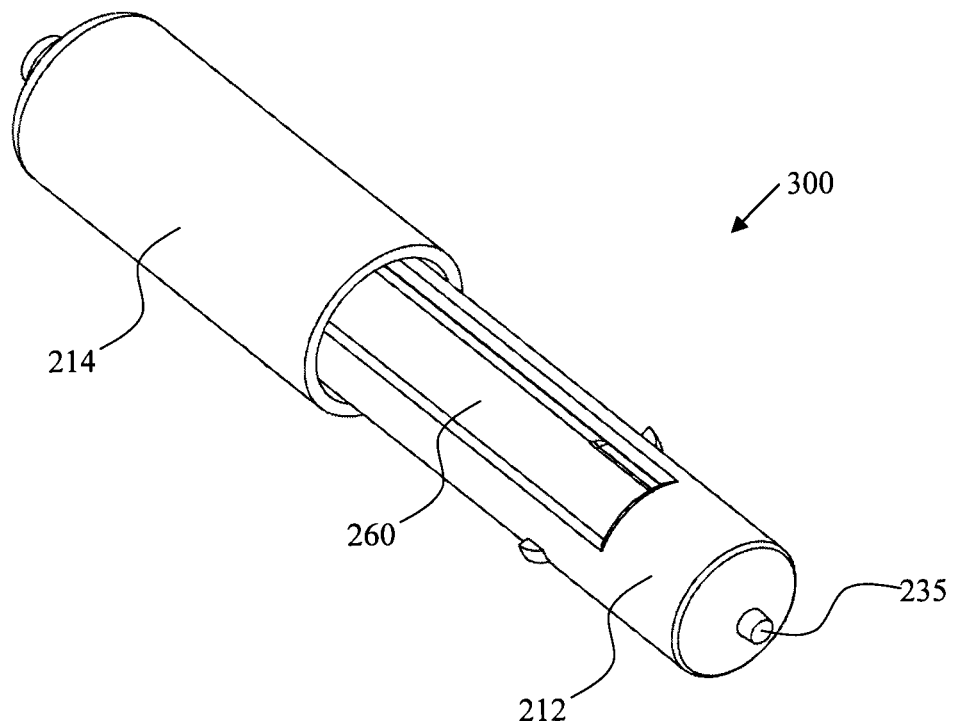
FIG. 13 is an illustration of a third embodiment of the present invention in which an isometric view of device 300 is presented.

Referring to FIG. 11, when first piston 222 engages second piston 224, the reservoir 220 is exhausted. In this case, additional pushing of the second end 214 is prevented.

Reference is now made to FIGS. 14-18, which schematically illustrate another embodiment of the present invention. According to these figures, active agent delivery device 400 comprises the following components:
a. A housing 310 with a first end 312 and a second end 314. Housing 310 comprises a reservoir 320 which is configured for storing an active agent.
b. An applicator 330 located at first end 312 of housing 310. The applicator 330 is adapted to incorporate a delivery tip 335 (illustrated in FIGS. 15-16). The delivery tip 335 is adapted to be in fluid communication with reservoir 320. Channel 350 is adapted to create fluid communication between delivery tip 335 and reservoir 320.
c. An active agent delivery mechanism 340 mechanically connected to reservoir 320. The active agent delivery mechanism 340 is adapted to deliver a predetermined amount of active agent (not shown) to delivery tip 335.

According to certain embodiments of the present invention, delivery tip 335 is a made of substantially porous and substantially rigid material adapted to delay passage of the predetermined amount of the active agent through delivery tip 335. When the predetermined amount of the active agent delivered to delivery tip 335, the delivery tip is adapted to: (i) absorb at least part of the predetermined amount of the active agent; and (ii) discharge at least part of the predetermined amount of the active agent upon a contact of delivery tip 335 with the subject's tissue.

Figure 14:
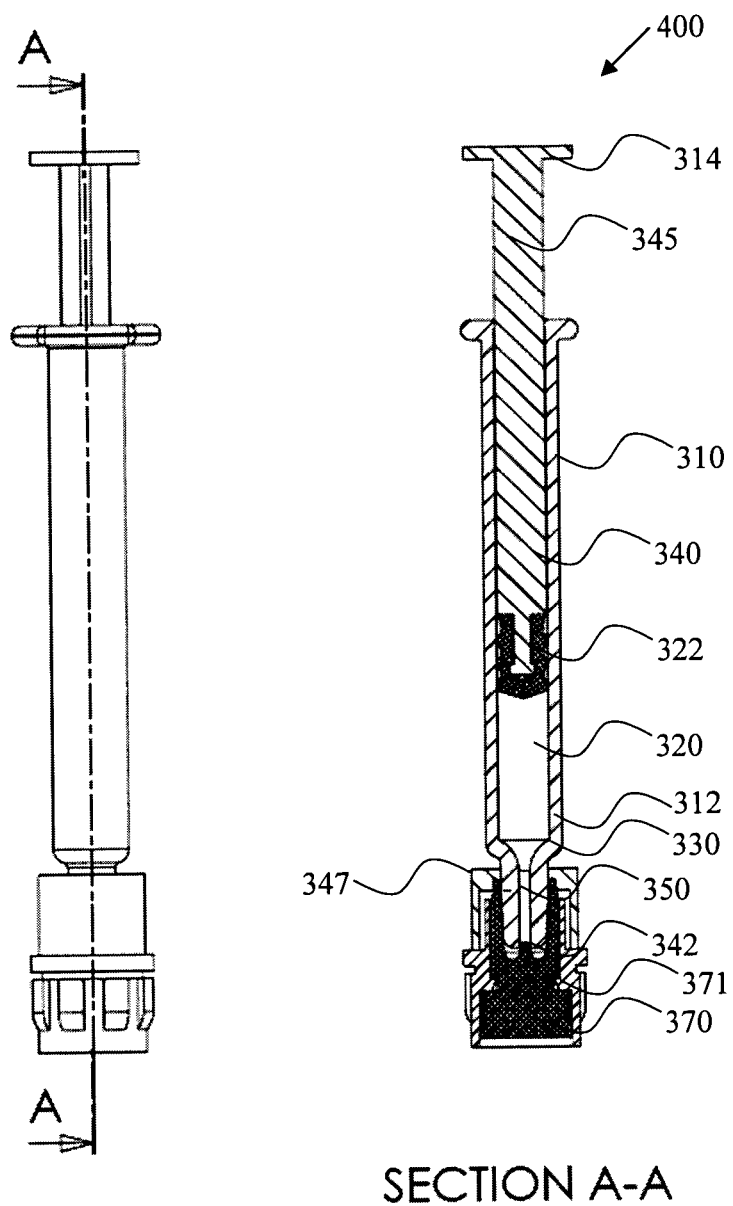
FIG. 14 is an illustration of a fourth embodiment of the present invention in a position which the device 400 is before usage. In this Figure only part of the device is shown.

Referring to FIG. 14, hub 342 is adapted to be covered with a soft cap 370. The soft cap 370 is adapted to prevent delivery of the active agent out of device 400.

According to a specific embodiment, hub 342 is constructed of a male Luer Lock 347 which is assembled on first end 312 of housing 310. Soft cap 370 may be connected to male Luer Lock 347 via female Luer Lock 371. At this position the active agent is kept sterile during storage until use. Before application of the active agent, the user removes cap assembly 370 and replaces it with assembly 339 including tip 335, female luer lock 348 and protecting cap 337.

Figure 15:
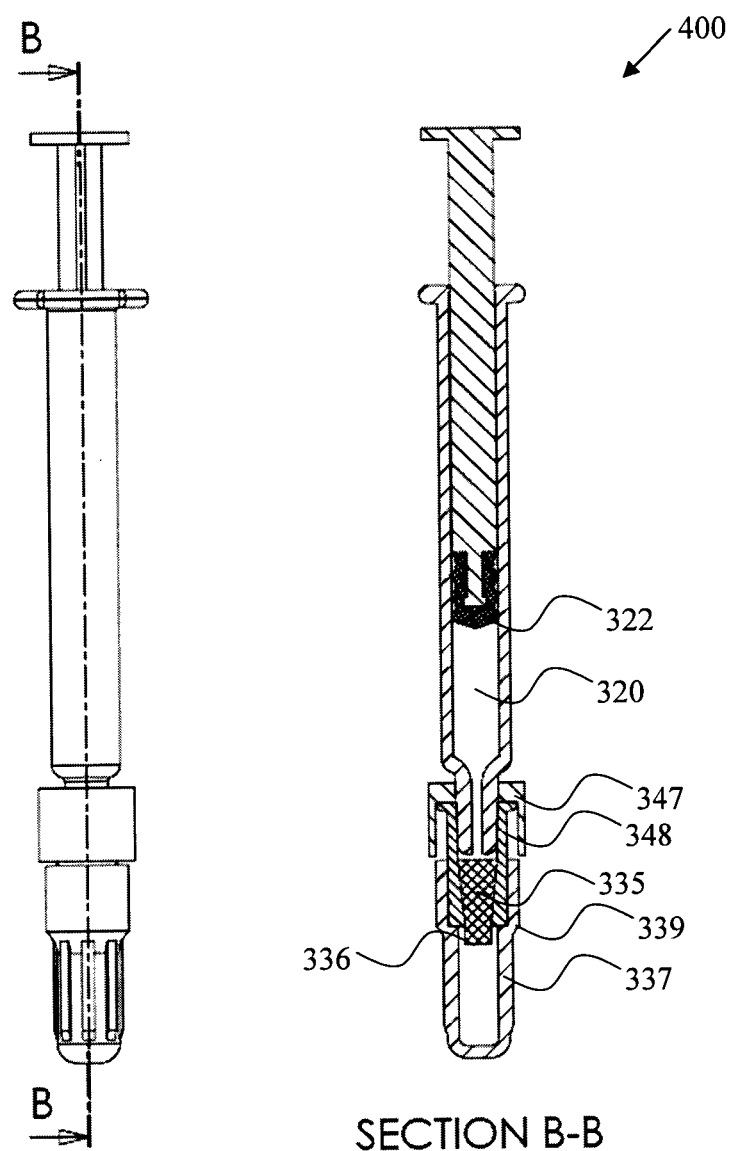
FIG. 15 is an illustration of a fourth embodiment of the present invention in a position in which the device 400 is ready to be used or is primed for use.
Figure 16:
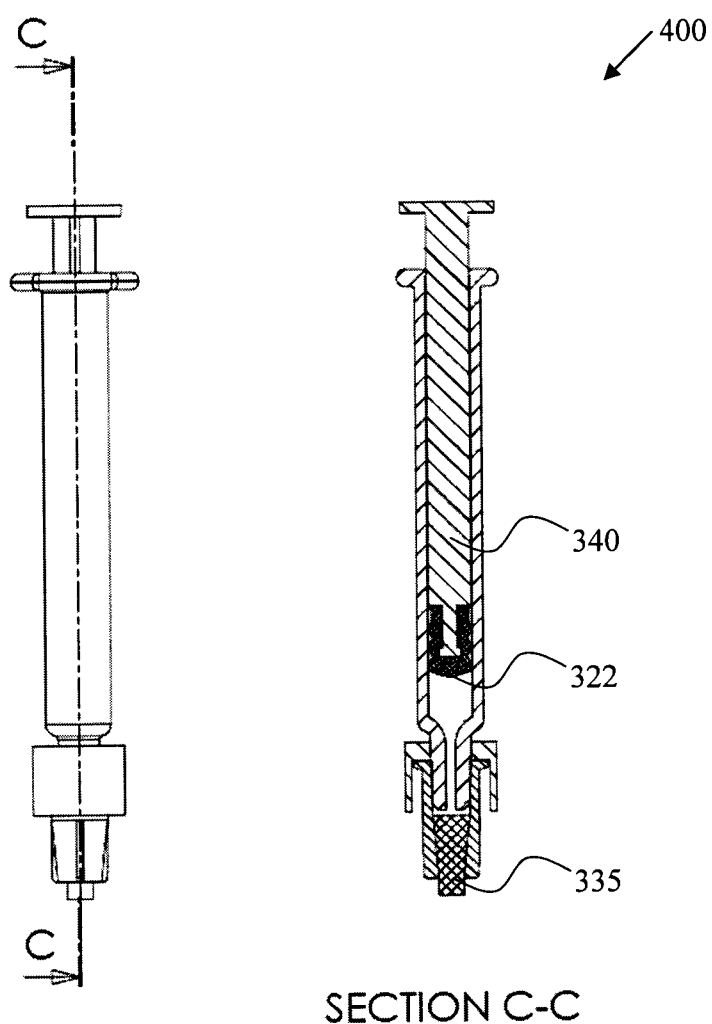
FIG. 16 is an illustration of a fourth embodiment of the present invention in a position in which the device 400 is used.
Figure 17:
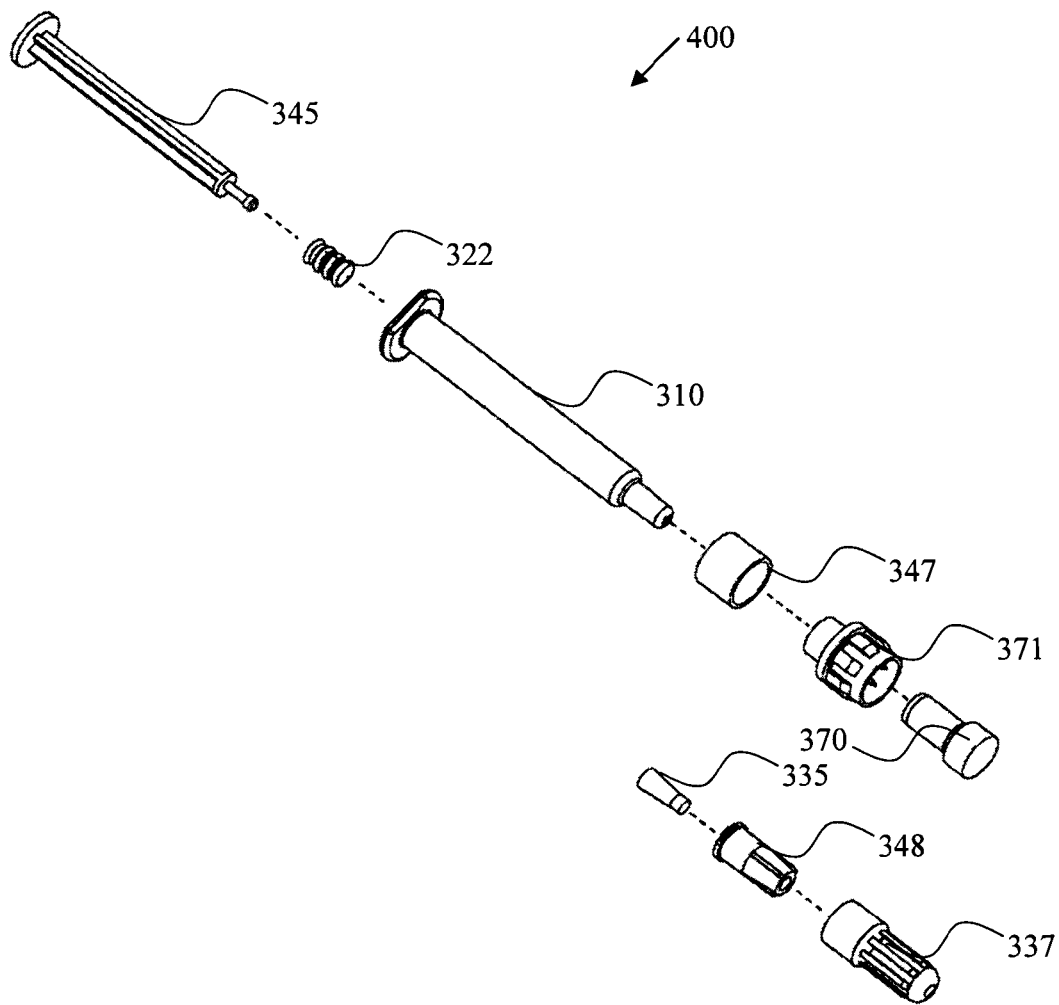
FIG. 17 is an illustration of a fourth embodiment of the present invention in which the elements of device 400 are presented in exploded view.
Figure 18:
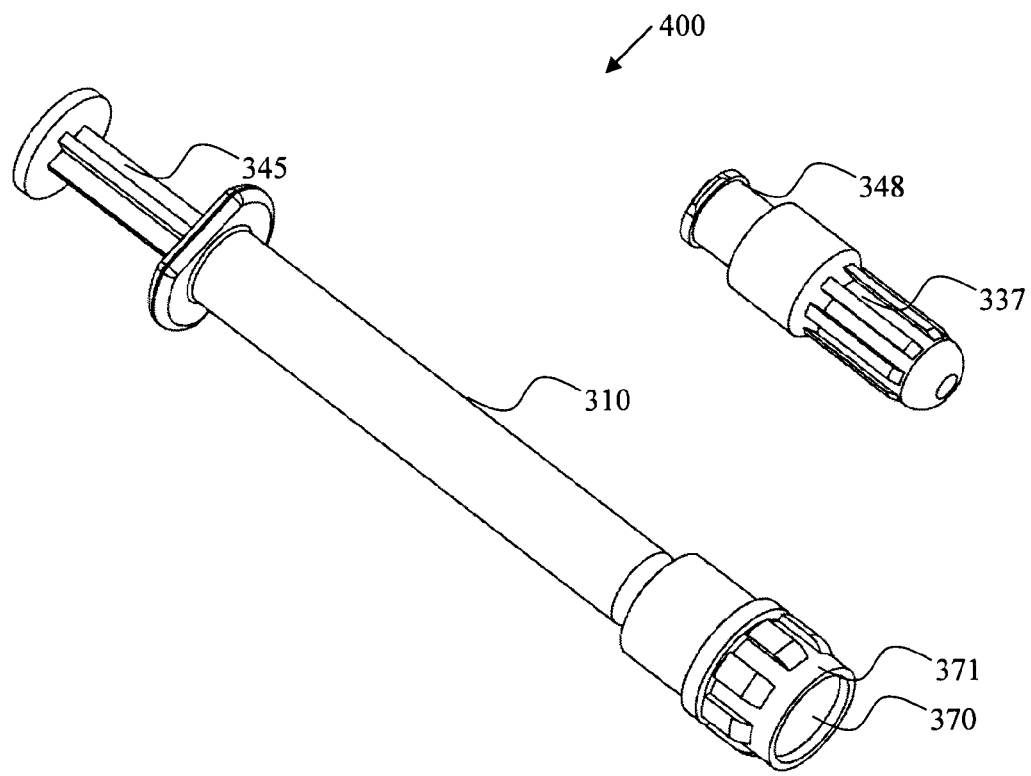
FIG. 18 is an illustration of a fourth embodiment of the present invention in which an isometric view of device 400 is presented.
Figure 19:
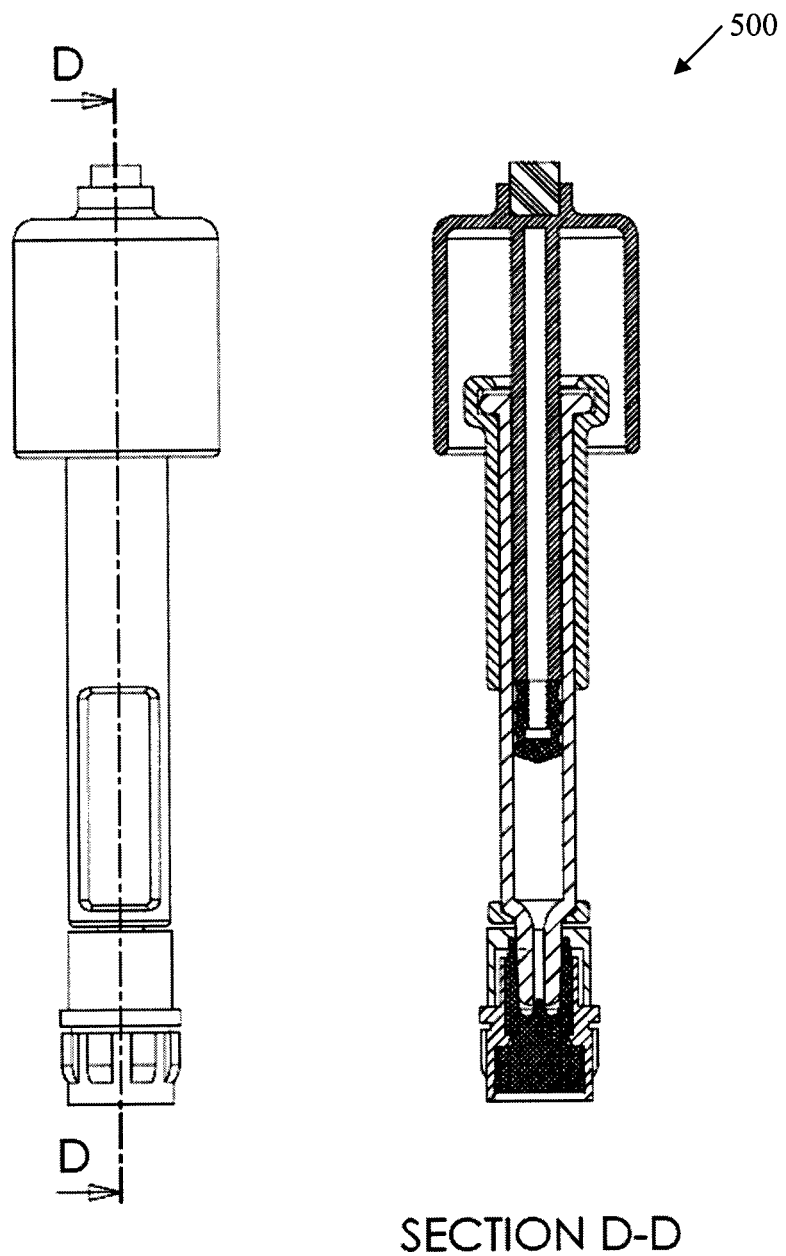
FIG. 19 is an illustration of a fifth embodiment of the present invention in a position which the device 500 is before usage.
Figure 20:
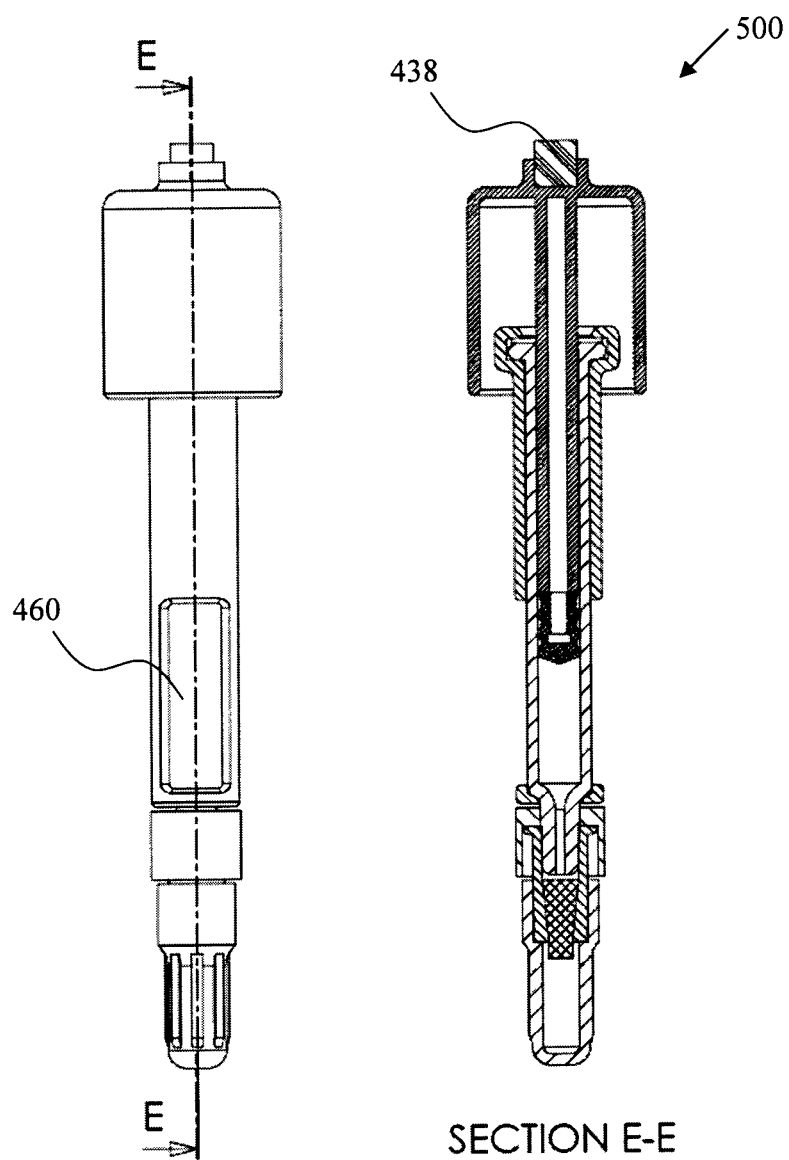
FIG. 20 is an illustration of a fifth embodiment of the present invention in a position in which the device 500 is ready to be used.
Figure 21:
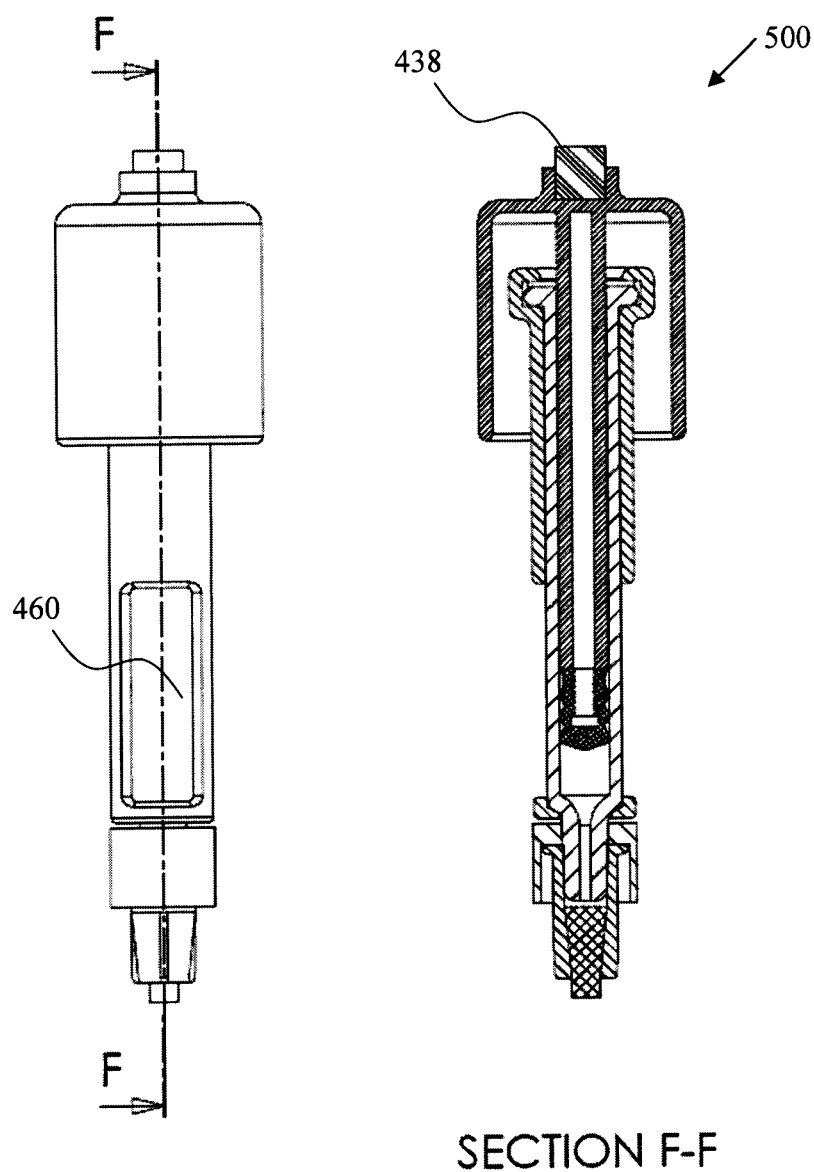
FIG. 21 is an illustration of a fifth embodiment of the present invention in a position in which the device 500 is used.
Figure 22:
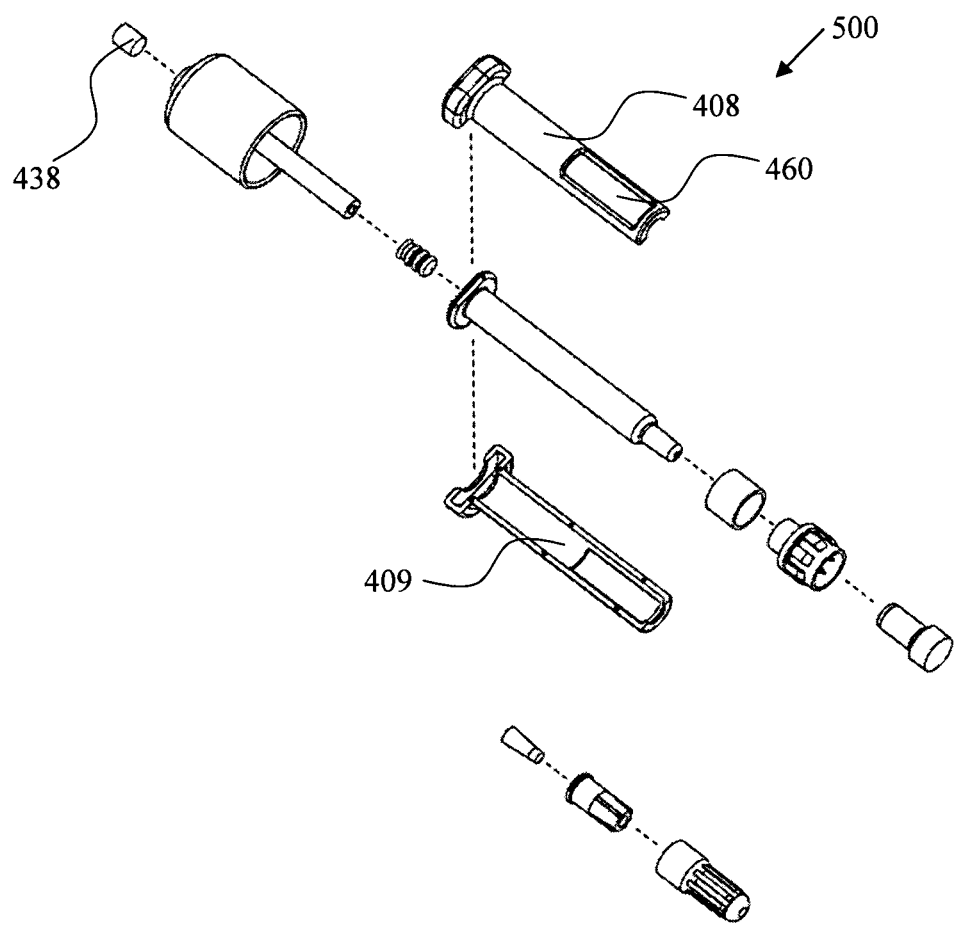
FIG. 22 is an illustration of a fifth embodiment of the present invention in which the elements of device 500 are presented in exploded view.
Figure 23:
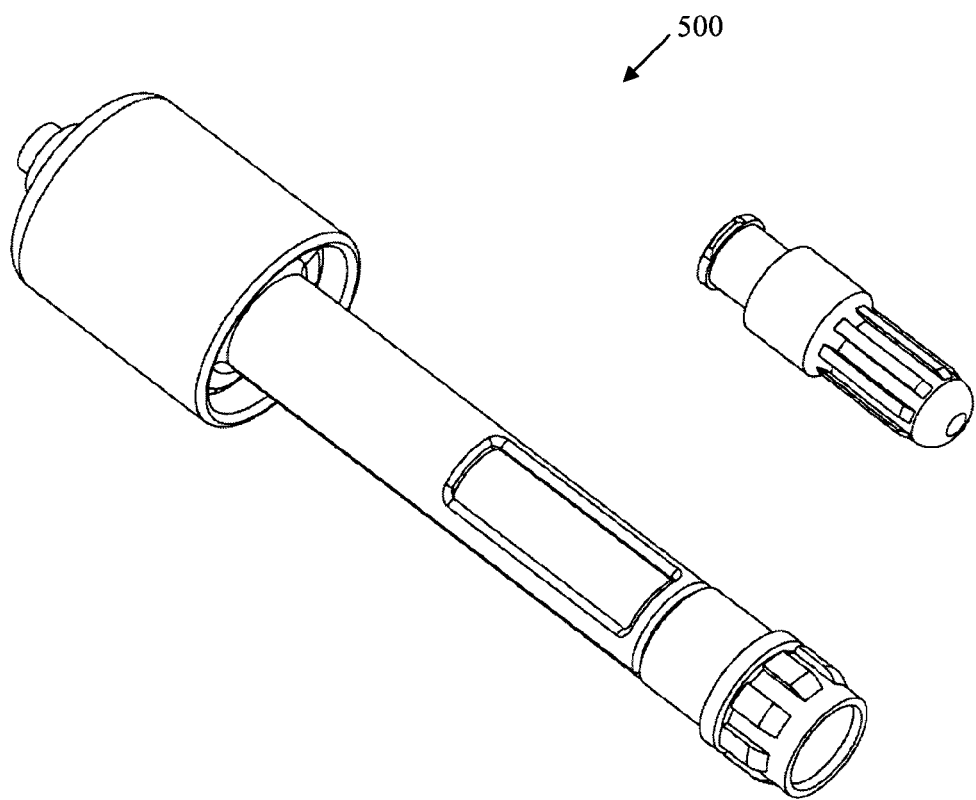
FIG. 23 is an illustration of a fifth embodiment of the present invention in which a side view of device 500 is presented.

According to FIGS. 15-16, hub 342 incorporates delivery tip 335 instead of cap 370. Delivery tip 335 may connected to male Luer Lock 347 via female Luer Lock 348.

According to this embodiment, active agent delivery mechanism 340 comprises a plunger 345 located within and connected to second end 314.

According to the specific embodiment of FIG. 15, reservoir 320 comprises a first piston 322. First piston 322 and delivery tip 335 are spaced apart creating in between a sealed chamber which may contain the active agent.

In operation, as illustrated in FIG. 15, following the removal of a protecting cap 337, the device may be used. By pushing second end 314 of housing 310 towards first end 312, plunger 345 pushes first piston 322 towards delivery tip 335. The pushing of first piston 322 actuates pushing forces on the active agent within reservoir 320. The pushing forces are adapted to force the predetermined amount of the active agent to be delivered to delivery tip 335. By further movement of second end 314 towards delivery tip 335, the active agent is forced to flow towards delivery tip 335. As a result of that, delivery tip 335 absorbs at least part of the predetermined amount of the active agent, and is ready to deliver the same to the tissue of the subject by using wetting side 336 of delivery tip 335 which is saturated with the active agent. For delivering the active agent to the subject's tissue, wetting end 336 of delivery tip 335 is applied on the subject's tissue (by contact). This results with discharging the active agent on the subject's tissue while the user of device 400 holds the device by hand. In order to assist penetration of the active agent to the patient's tissue, pressure on the tissue may be applied by using wetting end 336 of delivery tip 335. When delivery tip 335 dries, further pushing of second end 314 towards first end 312 will cause delivery tip 335 to absorb additional portion of the active agent, and to be saturated again.

Reference is now made to FIGS. 19-23 which schematically illustrate another embodiment of the present invention. According to this embodiment, the main elements of active agent delivery device 500 are similar to the element of active agent delivery device 400. The main differences between the embodiment of device 400 and the embodiment of device 500 are: in the construction of housing 410 which is made of two elements (408 and 409) and comprises an inspection window 460; and a chip 438 (as in the embodiments described above).

Reference is now made to FIGS. 24-28, which schematically illustrate another embodiment of the present invention. According to these figures, active agent delivery device 600 comprises the following components:
a. A housing 510 with a first end 512 and a second end 514.
   Housing 510 comprises a reservoir 520 which is configured for storing an active agent.
b. An applicator 530 located at first end 512 of housing 510.
   The applicator 530 is adapted to incorporate a delivery tip 535. The delivery tip 535 is adapted to be in fluid communication with reservoir 520. Delivery tip 535 is placed in hub 542. Hub 542 is assembled on housing a middle portion 513 of housing 510, such that snaps 517 are located in housing first notch 514. A channel 550 is adapted to create fluid communication between delivery tip 535 and reservoir 520.
c. An active agent delivery mechanism 540 mechanically connected to reservoir 520. The active agent delivery mechanism 540 is adapted to deliver a predetermined amount of active agent (not shown) to delivery tip 535.

According to certain embodiments of the present invention, delivery tip 535 is a made of substantially porous and substantially rigid material adapted to delay passage of the predetermined amount of the active agent through delivery tip 535. When the predetermined amount of the active agent delivered to delivery tip 535, the delivery tip is adapted to: (i) absorb at least part of the predetermined amount of the active agent; and (ii) discharge at least part of the predetermined amount of the active agent upon a contact of delivery tip 535 with the subject's tissue.

According to the specific embodiment of the present invention, the active agent delivery mechanism is adapted to control the passage of active agent from reservoir 520 and to delivery tip 535. As part of the control, active agent delivery mechanism may establish or prevent fluid communication between delivery tip 535 and reservoir 220. This may be performed via an elastomeric stopper 551 which may be located between reservoir 520 and delivery tip 535 within channel 550, such that when elastomeric stopper 551 is punctured via a spike 552, a fluid communication between reservoir 520 and delivery tip 535 is established. Elastomeric stopper 551 is sealingly engaged to channel 550 and secured by crimped aluminum cover 554. According to this embodiment, spike 552 is a sharpened tube through which the active agent from reservoir 520 is provided to delivery tip 535.

According to this embodiment, active agent delivery mechanism 540 comprises a plunger 545 located within and connected to second end 514. Plunger 545 may be screwed into second end 514 of housing 510.

Figure 24:
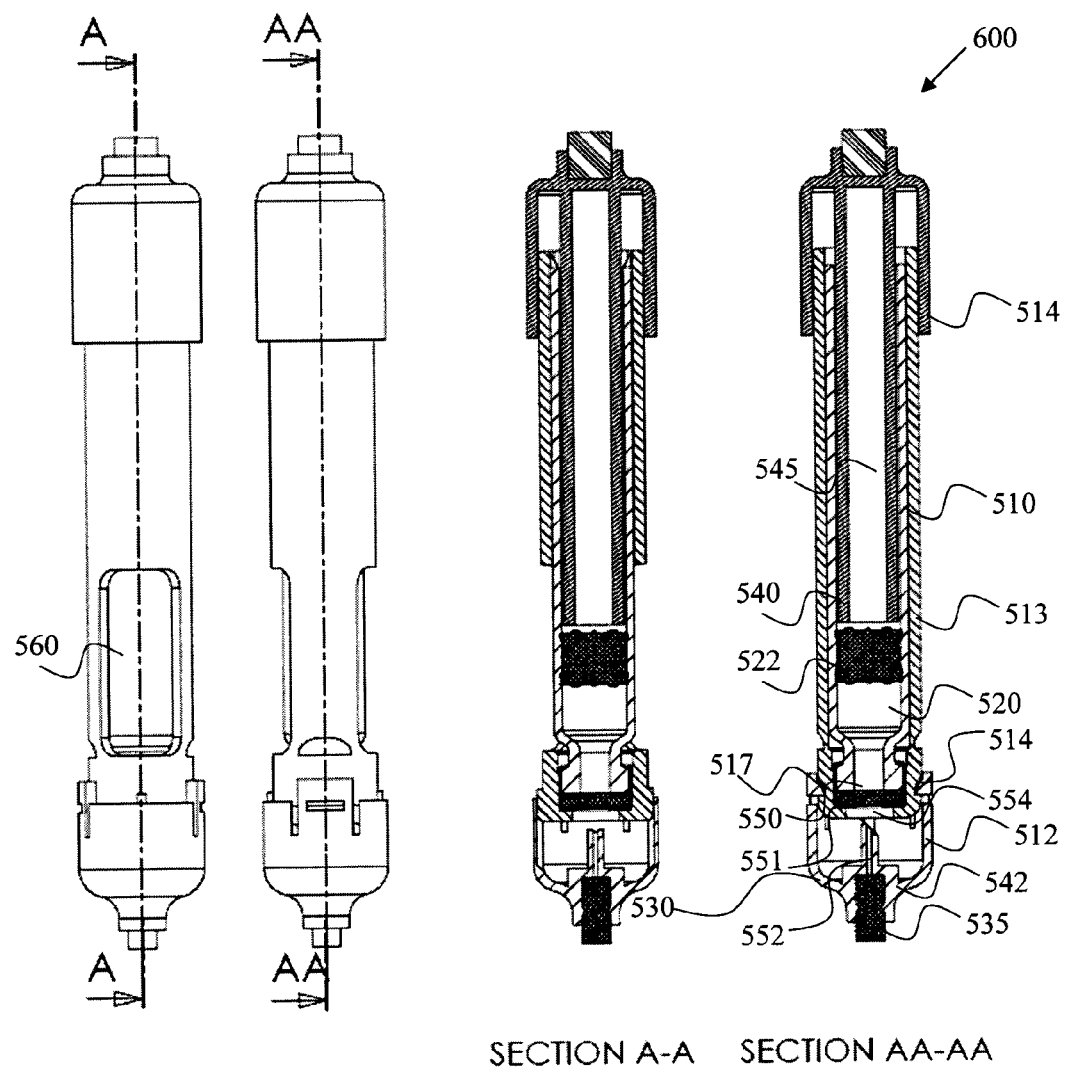
FIG. 24 is an illustration of a sixth embodiment of the present invention in a position which the device 600 is before usage.

According to the specific embodiment of FIG. 24, reservoir 520 comprises a first piston 522. First piston 522 and elastomeric stopper 551 are spaced apart creating in between a sealed chamber which may contain the active agent. According to this embodiment, reservoir 520 may be assembled into middle portion 513 of housing 510 and fixed within the same, thereby preventing axial movement of reservoir 520 relative to housing 510.

As can be seen in FIG. 24, before operation, elastomeric stopper 551 is distanced from spike 552. In this position, there is no fluid communication between the reservoir 520 and delivery tip 535. Inspection window 560 in housing 510 enables view of the active agent in reservoir 520.

Figure 25:
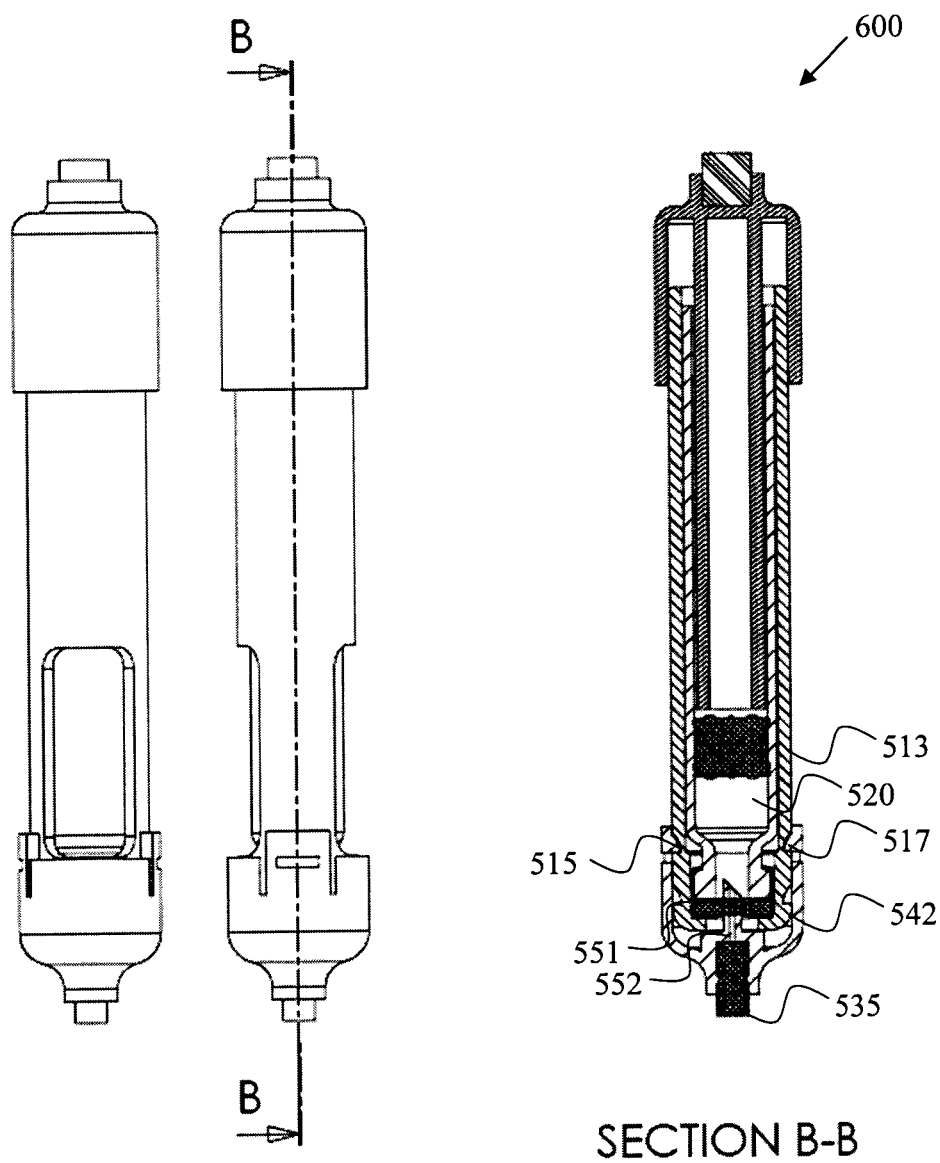
FIG. 25 is an illustration of a sixth embodiment of the present invention in a position in which the device 600 is ready to be used or is primed for use.

In preparation for operation, as illustrated in FIG. 25, hub 542 is pressed towards the direction of middle portion 513 of housing 510, and snaps 517 are integrate into housing second notch 515. As a result of that, spike 552 punctures elastomeric stopper 551, and penetrates into the same. This results in establishment of a fluid communication between reservoir 520 and delivery tip 535.

Figure 26:
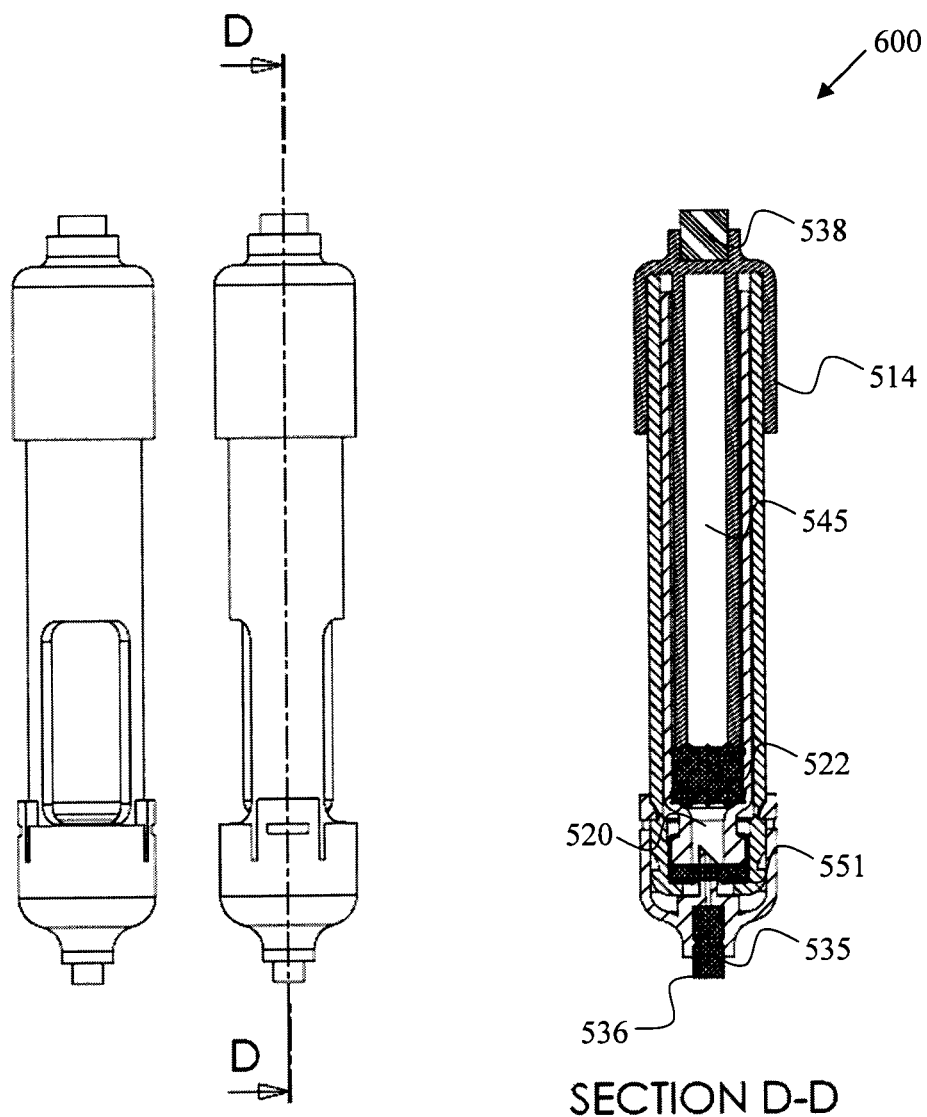
FIG. 26 is an illustration of a sixth embodiment of the present invention in a position in which the device 600 is used or its usage is terminated.
Figure 27:
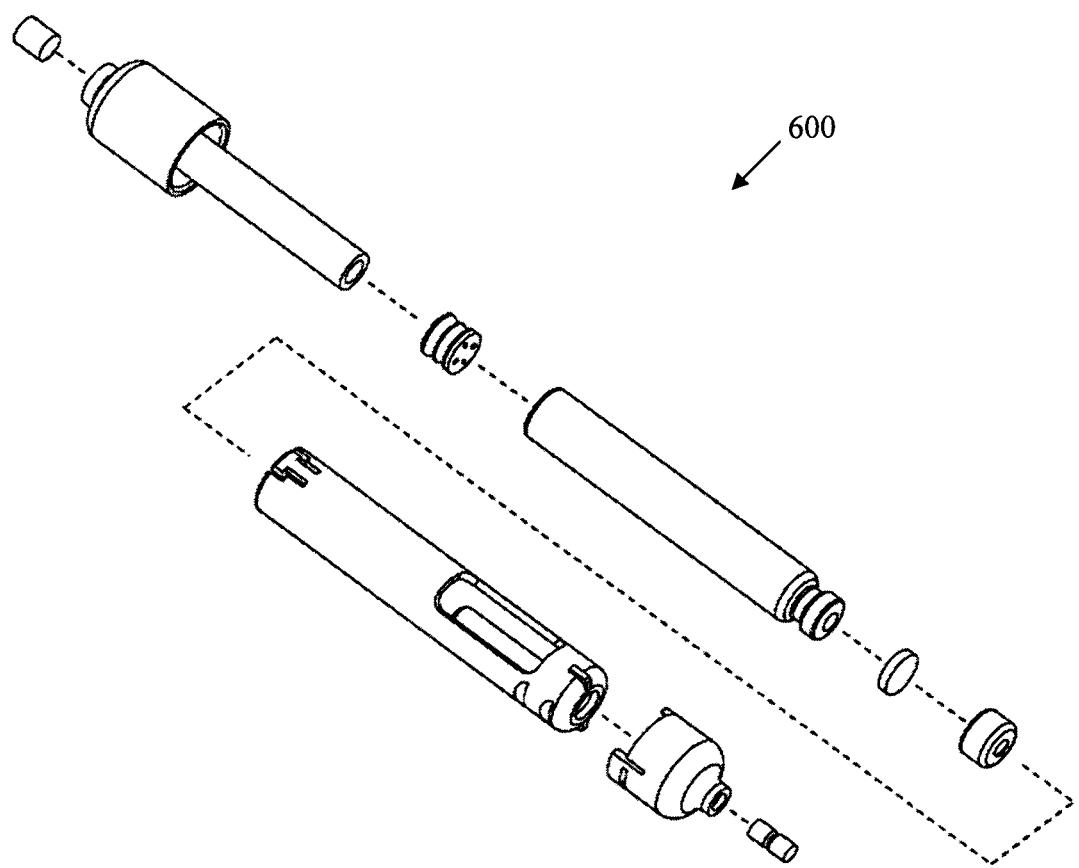
FIG. 27 is an illustration of a sixth embodiment of the present invention in which the elements of device 600 are presented in exploded view; and, FIG. 28 is an illustration of a sixth embodiment of the present invention in which an isometric of device 600 is presented.
Figure 28:
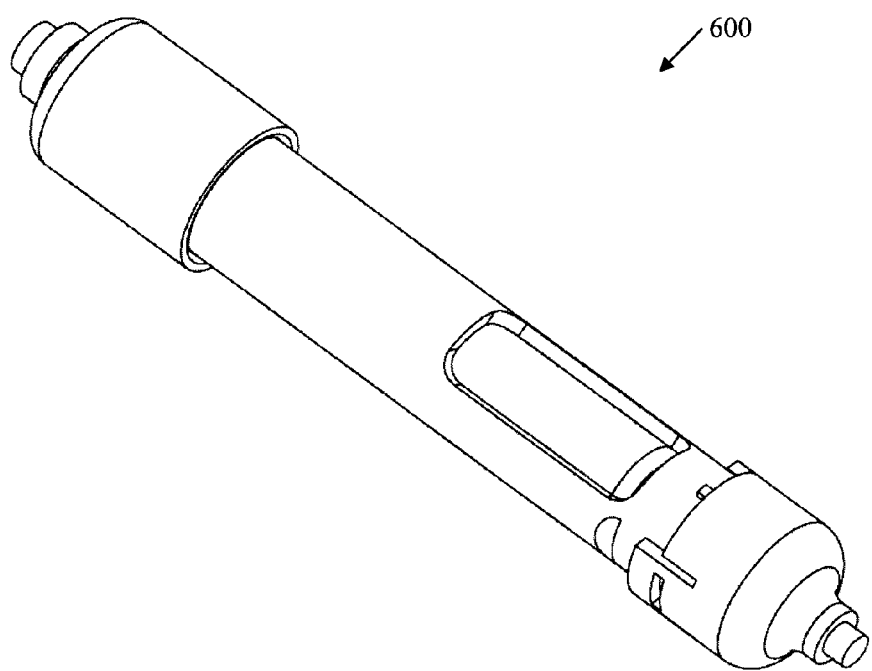

In operation, as illustrated in FIG. 26, by pushing second end 514 of housing 510 towards first end 512, plunger 545 pushes first piston 522 towards elastomeric stopper 551. The pushing of first piston 522 actuates pushing forces on the active agent within reservoir 520. The pushing forces are adapted to force the predetermined amount of the active agent to be delivered to delivery tip 535. As a result of that, delivery tip 535 absorbs at least part of the predetermined amount of the active agent, and is ready to deliver the same to the tissue of the subject by using wetting side 536 of delivery tip 535 which is saturated with the active agent. For delivering the active agent to the subject's tissue, wetting end 536 of delivery tip 535 is applied on the subject's tissue (by contact). This results with discharging the active agent on the subject's tissue while the user of device 600 holds the device by hand. In order to assist penetration of the active agent to the patient's tissue, pressure on the tissue may be applied either by using wetting end 536 of delivery tip 535, or by using chip 538. When delivery tip 535 dries, further pushing of second end 514 towards first end 512 will cause delivery tip 535 to absorb additional portion of the active agent, and to be saturated again.

According to different embodiment of the present invention, the pushing forces which are actuated on the active agent are associated with hydraulic pressure which causes the active agent to move from place to place.

The present invention also discloses a method for delivering an active agent to be applied to a tissue of a subject. The method comprises steps of:

a. providing an active agent delivery device adapted to be applied to a tissue of a subject, comprising: (i) a housing with a first end and a second end, the housing comprising a reservoir for storing an active agent; (ii) an applicator located at the first end of the housing, the applicator is adapted to incorporate a delivery tip adapted to be in fluid communication with the reservoir; and, (iii) an active agent delivery mechanism mechanically connected to the reservoir; the delivery tip being a made of substantially porous and substantially rigid material adapted to delay a passage of the predetermined amount of the active agent through the delivery tip;
b. connecting the delivery tip to the applicator;
c. delivering a predetermined amount of the active agent to the delivery tip via the active agent delivery mechanism;
d. absorbing at least part of the predetermined amount of the active agent in the delivery tip; and,
e. discharging at least part of the predetermined amount of the active agent upon a contact of the delivery tip with the tissue, thereby treating the tissue of the subject.

According to certain embodiments, the method for delivering an active agent as defined above, further comprises a step of selecting the material of the delivery tip from the group consisting of: wood, sponge/foam, felt, nylon, PTFE, Teflon®, PVDF, fluoropolymers, thermoplastic, thermoset and any combination thereof.

According to certain embodiments, the method for delivering an active agent as defined above, the active agent delivery mechanism comprises a plunger.

According to certain embodiments, the method for delivering an active agent as defined above, the step (c) of delivering a predetermined amount of the active agent to the delivery tip further comprising step of actuating pushing forces on the active agent via the plunger.

According to certain embodiments, the method for delivering an active agent as defined above, further comprises steps of: providing the device with a first piston located between the plunger and the active agent, and actuating pushing forces on the active agent via the plunger and the piston.

According to certain embodiments, the method for delivering an active agent as defined above, further comprises steps of: providing the device with a second piston located within the reservoir between the active agent and the delivery tip, and controlling passage of the active agent to the delivery tip via the second piston.

According to certain embodiments, the method for delivering an active agent as defined above, further comprises step of applying the pushing forces on the second piston, thereby moving the second piston within the reservoir to provide a bypass to the active agent.

According to certain embodiments, the method for delivering an active agent as defined above, the delivery tip is adapted to be in fluid communication with the reservoir though a channel.

According to certain embodiments, the method for delivering an active agent as defined above, the plunger is located between the delivery tip and the reservoir.

According to certain embodiments, the method for delivering an active agent as defined above, the channel is extending within the plunger.

According to certain embodiments, the method for delivering an active agent as defined above, the channel is a needle.

According to certain embodiments, the method for delivering an active agent as defined above, further comprises step of controlling the passage of the active agent from the reservoir and to the delivery tip via the active agent delivery mechanism.

According to certain embodiments, the method for delivering an active agent as defined above, further comprises steps of: providing the active agent delivery mechanism with a knob, and controlling the operation of the active agent delivery mechanism via the knob.

According to certain embodiments, the method for delivering an active agent as defined above, further comprises step of providing the device with a chip located at the second end of the housing, the chip being adapted to be used for spreading the active agent on the tissue following the delivery of the active agent to the tissue via the delivery tip.

According to certain embodiments, the method for delivering an active agent as defined above, further comprises a step of selecting the material of the chip from the group consisting of: wood, sponge/foam, felt, nylon, PTFE, Teflon®, PVDF, fluoropolymers, thermoplastic, thermoset and any combination thereof.

According to certain embodiments, the method for delivering an active agent as defined above, further comprises a step of providing information regarding the amount of the active agent within the reservoir via an inspection window.

According to certain embodiments, the method for delivering an active agent as defined above, further comprises a step of providing indication regarding the fluid communication of the reservoir with the delivery tip via the inspection window.

According to certain embodiments, the method for delivering an active agent as defined above, further comprises a step of connecting a cap to the applicator in stead of the delivery tip, thereby preventing delivery of the active agent out of the device.

According to certain embodiments, the method for delivering an active agent as defined above, the active agent comprises substances selected from the group consisting of: trichloroacetic acid, formic acid, and any combination thereof.

According to certain embodiments, the method for delivering an active agent as defined above, the device is adapted for treating tissue lesions.

According to certain embodiments, the method for delivering an active agent as defined above, further comprises steps of: providing said active agent delivery mechanism with an elastomeric stopper adapted to be located between said reservoir and said delivery tip; and, puncturing said elastomeric stopper via a spike, thereby establishing a fluid communication between said reservoir and said delivery tip.

The invention claimed is:

1. A device for delivering an active agent to a tissue, comprising:
   a. a housing with a first end and a second end, including a reservoir comprising a first piston and second piston spaced apart forming a sealed chamber for containing said active agent;
   b. a delivery tip located in said first end of said housing in fluid communication with said reservoir when actuated; and,
   c. a delivery mechanism capable of delivering a predetermined amount of said active agent and releasing the same upon contact between said delivery tip and said tissue;
   d. a chip located in said second end of said housing, wherein said chip is adapted for actuating a predetermined pressure on said tissue to force the penetration of said active agent;

wherein said delivery mechanism comprises a rotational mechanism adapted to control the operation of said delivery mechanism by audible sound or sudden reduction in rotational friction force;

further wherein said fluid communication between said delivery tip and said reservoir is absent before actuation of said device.

2. The device according to claim 1, wherein said delivery tip is made of substantially porous and substantially rigid material adapted to delay passage of said predetermined amount of said active agent through said delivery tip; further wherein said delivery tip is adapted to: (i) absorb at least part of said predetermined amount of said active agent; and (ii) discharge at least part of said predetermined amount of said active agent upon a contact of said delivery tip with said tissue.

3. The device according to claim 1, wherein said delivery mechanism comprises a plunger.

4. The device according to claim 3, wherein said plunger is adapted to actuate pushing forces on said active agent, said pushing forces are adapted to force said predetermined amount of said active agent to be delivered to said delivery tip.

5. The device according to claim 4, wherein said plunger is adapted to actuate said pushing forces on said active agent said via a first piston located between said plunger and said active agent.

6. The device according to claim 4, wherein said delivery tip is adapted to be in fluid communication with said reservoir though a channel.

7. The device according to claim 4, wherein said plunger is located between said delivery tip and said reservoir.

8. The device according to claim 6, wherein said channel extends within said plunger.

9. The device according to claim 6, wherein said channel is a needle.

10. The device according to claim 1, wherein said delivery mechanism is further adapted to control the passage of said active agent from said reservoir and to said delivery tip.

11. The device according to claim 1, further comprising an inspection window for providing information regarding the amount of said active agent within said reservoir.

12. The device according to claim 11, wherein said inspection window is adapted to provide indication regarding the fluid communication of said reservoir with said delivery tip.

* * * * *